US008771940B2

(12) United States Patent
Andersen et al.

(10) Patent No.: US 8,771,940 B2
(45) Date of Patent: Jul. 8, 2014

(54) ARRAY FOR DETECTING MICROBES

(75) Inventors: Gary L. Andersen, Berkeley, CA (US); Todd D. DeSantis, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 531 days.

(21) Appl. No.: 12/474,204

(22) Filed: May 28, 2009

(65) Prior Publication Data
US 2009/0291858 A1 Nov. 26, 2009

Related U.S. Application Data

(63) Continuation of application No. PCT/US2007/024720, filed on Nov. 29, 2007.

(60) Provisional application No. 60/861,834, filed on Nov. 30, 2006.

(51) Int. Cl.
C12Q 1/68 (2006.01)
C12P 19/34 (2006.01)
C12M 1/34 (2006.01)
C07H 21/02 (2006.01)

(52) U.S. Cl.
USPC ....... 435/6.1; 435/91.2; 435/287.1; 536/23.1; 536/24.3

(58) Field of Classification Search
USPC .................... 435/6; 536/23.1, 24.3
See application file for complete search history.

(56) References Cited

U.S. PATENT DOCUMENTS

| | | | | |
|---|---|---|---|---|
| 5,874,291 A * | 2/1999 | Bielefeldt et al. | ............ | 435/262 |
| 6,156,501 A | 12/2000 | McGall et al. | | |
| 6,228,575 B1 | 5/2001 | Gingeras et al. | | |
| 6,261,776 B1 | 7/2001 | Pirrung et al. | | |
| 6,309,823 B1 | 10/2001 | Cronin et al. | | |
| 6,607,887 B2 | 8/2003 | Chee | | |
| 6,913,879 B1 | 7/2005 | Schena | | |
| 7,108,968 B2 | 9/2006 | Gingeras et al. | | |
| 7,115,364 B1 | 10/2006 | Chee et al. | | |
| 7,214,492 B1 * | 5/2007 | Rublee et al. | ...................... | 435/6 |
| 7,455,966 B1 * | 11/2008 | Schaudies et al. | ................ | 435/6 |
| 2001/0053519 A1 * | 12/2001 | Fodor et al. | ........................ | 435/6 |
| 2002/0086289 A1 * | 7/2002 | Straus | ................................ | 435/6 |
| 2002/0187490 A1 | 12/2002 | Tiedje et al. | | |
| 2004/0110183 A1 | 6/2004 | Ashby | | |
| 2005/0170361 A1 * | 8/2005 | Ho et al. | ............................ | 435/6 |
| 2005/0191656 A1 * | 9/2005 | Drmanac et al. | ................... | 435/6 |
| 2006/0046246 A1 | 3/2006 | Zeng et al. | | |
| 2006/0058967 A1 | 3/2006 | Kwon et al. | | |
| 2006/0110744 A1 | 5/2006 | Sampas et al. | | |
| 2007/0269813 A1 | 11/2007 | Dewhirst et al. | | |
| 2008/0139398 A1 | 6/2008 | Ahn et al. | | |
| 2008/0280331 A1 | 11/2008 | Davies et al. | | |
| 2009/0030925 A1 | 1/2009 | Ozer | | |
| 2009/0054249 A2 * | 2/2009 | Ohlbaum et al. | ................... | 506/9 |
| 2009/0291854 A1 | 11/2009 | Wiesinger-Mayr et al. | | |
| 2011/0008791 A1 * | 1/2011 | Rothman et al. | ................... | 435/6 |
| 2011/0027782 A1 * | 2/2011 | Haake et al. | ....................... | 435/6 |
| 2011/0053802 A1 * | 3/2011 | Forney et al. | ................... | 506/16 |

FOREIGN PATENT DOCUMENTS

| | | |
|---|---|---|
| WO | WO 99/22023 A2 | 5/1999 |
| WO | WO 2007/018563 A2 | 2/2007 |
| WO | WO 2007/039319 A2 | 4/2007 |

OTHER PUBLICATIONS

Bavykin et al. Portable System for microbial sample preparation and oligonucleotide microarray analysis. Applied and Environmental Microbiology 67 (2): 922-928 (2001).*
Bavykin et al., Portable system for microbial sample preparation and oligonucleotide microarray analysis. Applied and Environmental Microbiology 67 (2): 922-928 (2001).*
Guschin et al., Oligonucleotide microchips as genosensors for determinative and environmental studies in microbiology. Applied and Environmental Microbiology 63 (6): 2397-2402 (1997).*
Cho et al., Bacterial Species Determination from DNA-DNA Hybridization by Using Genome Fragments and DNA Microarrays. Applied and Environmental Microbiology 67 (8): 3677-3682 (2001).*
Gingeras et al. Simultaneous Genotyping and Species Identification Using Hybridization Pattern Recognition Analysis of Generic Mycobacterium DNA Arrays. Genome Research 8: 435-448 (1998).*
Loy et al., Oligonucleotide Microarray for 16S rRNA Gene-Based Detection of All Recognized Lineages of Sulfate-Reducing Prokaryotes in the Environment. Applied and Environmental Microbiology 68 (10): 5064-5081 (2002).*
Nelson et al., Label-free detection of 16S ribosomal RNA hybridization on reusable DNA arrays using surface plasmon resonance imaging. Environmental Microbiology 4(11): 735-743 (2002).*
Small et al., Direct detection of 16S rRNA in soil extracts by using oligonucleotide microarrays. Applied and Environmental Microbiology 67 (10): 4708-4716 (2001).*
Troesch et al., Mycobacterium species identification and rifampin resistance testing with high-density DNA probe arrays. J. of Clinical Microbiology 37 (1): 49-55 (1999).*
Loubinoux et al., Bacteremia Caused by a Strain of Desulfovibrio Related to the Provisionally Named Desulfovibrio fairfieldensis. J. of Clinical Microbiology 38(2): 931 (2000).*
Tee et al., Probable New Species of Desulfovibrio Isolated from a Pyogenic Liver Abscess. J. of Clinical Microbiology 34(7): 1760 (1996).*
Wison et al., Amplification of Bacterial 16S Ribosomal DNA with Polymerase Chain Reaction. J. of Clinical Microbiology 28(9): 1942 (1990).*
Torsvik et al. Prokaryotic Diversity—Magnitude, Dynamics, and Controlling Factors. Science 296:1064 (May 10, 2002.*
Heid et al. Real time quantitative PCR. Genome Research 6: 986 (1996).*

(Continued)

Primary Examiner — Stephan Kapushoc
(74) Attorney, Agent, or Firm — Knobbe, Martens, Olson & Bear LLP

(57) ABSTRACT

The present embodiments relate to an array system for detecting and identifying biomolecules and organisms. More specifically, the present embodiments relate to an array system comprising a microarray configured to simultaneously detect a plurality of organisms in a sample at a high confidence level.

28 Claims, 4 Drawing Sheets

(56) References Cited

OTHER PUBLICATIONS

Kirschner et al., Diagnosis of mycobacterial infections by nucleic acid amplification: 18-month prospective study. Journal of Clinical Microbiology 34 (2): 304 (1996).*

Zoetendal E.G. et al. J. Nutr. Feb. 1, 2004 vol. 134; No. 2; 465-472.*

Alexander Schliep et al., Group Testing With DNA Chips: Generating Designs and Decoding Experiments, Bioinformatics Conference, 2003. CSB 2003. Proceedings of the 2003 IEEE, pp. 1-8.*

Feng S. et al., A fast and flexible approach to oligonucleotide probe design for genomes and gene families. Bioinformatics. May 15, 2007;23(10):1195-1202.*

Krause A. et al. Accurate method for fast design of diagnostic oligonucleotide probe sets for DNA microarrays, Parallel and Distributed Processing Symposium, 2003. Proceedings, International, pp. 1-9.*

Alexander Schliep et al., Decoding non-unique oligonucleotide hybridization experiments of targets related by a phylogenetic tree, Bioinformatics. Jul. 15, 2006;22(14):e424-30.*

Peplies et al.: "A DNA Microarray Platform Based on Direct Detection of rRNA for Characterization of Freshwater Sediment-Related Prokaryotic Communities," Applied and Environmental Microbiology, vol. 72, pp. 4829-4838 (2006).

Peplies et al.: "Optimization Strategies for DNA Microarray-Based Detection of Bacteria with 16S rRNA-Targeting Oligonucleotide Probes," Applied and Environmental Microbiology, vol. 69, pp. 1397-1407 (2003).

Office Action dated Feb. 15, 2011 for European Patent Application No. 07874524.7, filed Nov. 29, 2007.

Adamczyk, et al. The isotope array, a new tool that employs substrate-mediated labeling of rRNA for determination of microbial community structure and function. Appl Environ Microbiol. Nov. 2003;69(11):6875-87.

Berkeley Lab Technology. PhyloChip: DNA microarray for rapid profiling of microbial populations. Available at http://www.lbl.gov/Tech-Transfer/techs/lbn12229.html. Accessed May 13, 2009.

De Saizieu, et al. Microarray-based identification of a novel *Streptococcus pneumoniae* regulon controlled by an autoinduced peptide. J Bacteriol. Sep. 2000;182(17):4696-703.

European search report dated May 7, 2010 for Application No. 7874524.7.

Guschin, et al. Oligonucleotide microchips as genosensors for determinative and environmental studies in microbiology. Appl Environ Microbiol. Jun. 1997;63(6):2397-402.

International search report dated Nov. 10, 2008 for PCT Application No. US2007/024720.

Polz, et al. A(r)Ray of hope in analysis of the function and diversity of microbial communities. Biol Bull. Apr. 2003;204(2):196-9.

Brodie et al., "Application of a high-density oligonucleotide microarray approach to study bacterial population dynamics during uranium reduction and reoxidation," *Appl. Environ. Microbiol.*, 72(9):6288-6298 (2006).

International Search Report and Written Opinion dated Nov. 10, 2008 for International Application No. PCT/US2007/024720, Filed Nov. 29, 2007.

International Preliminary Report on Patentability dated Jun. 3, 2009 for International Application No. PCT/US2007/024720, Filed Nov. 29, 2007.

Brodie et al., "Application of a High-Density Oligonucleotide Microarray Approach to Study Bacterial Population Dynamics During Uranium Reduction and Reoxidation," *Appl Environ Microbiol.*, 2006, 72(9):6288-6298.

Desantis et al., "Comprehensive Aligned Sequence Construction for Automated Design of Effective Probes (CASCADE-P) Using 16S rDNA, *Bioinformatics*," 2003, 19(12):1461-1468.

Desantis et al., "Rapid Quantification and Taxonomic Classification of Environmental DNA From Both Prokaryotic and Eukaryotic Origins Using a Microarray," *FEMS Microbiol Lett.*, 2005, 245(2):271-278.

Desantis et al., "Greengenes, a chimera-checked 16S rRNA gene database and workbench compatible with ARB," *Appl Environ Microbiol.*, 2006, 72(7):5069-5072.

Desantis et al., "High-Density Universal 16S rRNA Microarray Analysis Reveals Broader Diversity Than Typical Clone Library When Sampling The Environment," 2007, *Microb. Ecol.*, 53(3):371-383.

Ryder, "Researchers Find Pathogens in Unlikely Places Using High-density Microarrays", *Affymetrix Microarray Bulletin*, 2006, 2(1):4-8.

Wilson et al., "Sequence-specific identification of 18 pathogenic microorganisms using microarray technology," 2002, *Mol. Cell Probes.*, 16(2):119-127.

Wilson et al., "High-Density Microarray of Small-Subunit Ribosomal DNA Probes," *Appl Environ Microbiol.*, 2002, 68(5):2535-2541.

"Berkeley Lab Technology Could Help Areas Flooded by Katrina and Rita," *Berkeley Lab Research News*, Sep. 27, 2005.

Biello, "Microbe Census Reveals Air Crawling with Bacteria," ScientificAmerican.com, Dec. 19, 2006.

Bohannon, "Microbiology's Air Force," *ScienceNOW Daily News*, Dec. 20, 2006.

Brodie et al., "Urban aerosols harbor diverse and dynamic bacterial populations," *Proc Natl Acad Sci USA*, 2007, 104(1):299-304.

Cole et al., "The ribosomal database project (RDP-II): introducing myRDP space and quality controlled public data," *Nucleic Acids Res*, 2007, 35:D169-172.

Curtis et al., "Estimating prokaryotic diversity and its limits," *Proc Natl Acad Sci USA*, 2002, 99(16):10494-10499.

De Hoon et al., "Open source clustering software," *Bioinformatics*, 2004, 20(9):1453-1454.

Dunbar et al., "Empirical and theoretical bacterial diversity in four Arizona soils." *Appl Environ Microbiol*, 2002, 68:3035-3045.

Flanagan et al., "Loss of bacterial diversity during antibiotic treatment of intubated patients colonized with *Pseudomonas aeruginosa*," *J Clin Microbiol*, 2007, 45(6):1954-1962.

Gans et al., "Computational improvements reveal great bacterial diversity and high metal toxicity in soil," *Science*, 2005, 309(5739):1387-1390.

Hill et al., "Using ecological diversity measures with bacterial communities," *FEMS Microbiol Ecol*, 2003, 43(1):1-11.

Lin et al., "Long-Term Sustainability of a High-Energy, Low-Diversity Crustal Biome," *Science*, 2006, 314:479-482.

Lozupone et al., "UniFrac—an online tool for comparing microbial community diversity in a phylogenetic context," *BMC Bioinformatics*, 2006, 7:371.

Sagaram et al., "Bacterial Diversity Analysis of Huanglongbing Pathogen-Infected Citrus, Using PhyloChip Arrays and 16S rRNA Gene Clone Library Sequencing," *App. Environ. Microbiol.* 2009, 75:1566-1574.

Thacker, "A Nationwide Census of Airborne Bacteria," *Environmental Science & Technology*, 2004, 38(19):361A-362A.

United States International, "Surprise in airborne bacteria census," Dec. 19, 2006.

Wilson et al., "Amplification of Bacterial 16S Ribosomal DNA with Polymerase Chain Reaction," *J. Clin. Microbiol.*, 1990, 28:1942-1946.

Woese et al., "Phylogenetic structure of the prokaryotic domain: the primary kingdoms," *Proc Natl. Acad Sci USA*, 1977, 74:5088-5090.

European search and examination report dated Feb. 18, 2013 for EP Application No. 10792771.7.

Desantis et al., Comprehensive aligned sequence construction for automated design of effective probes (CASCADE-P) using 16S rDNA, Bioinformatics, 2003, vol. 19, No. 12.

Frank et al., Molecular-phylogenic characterization of microbial community imbalances in human inflammatory bowel diseases, PNAS, USA, 2007, vol. 104, No. 34, pp. 13780-13785.

Gentry, et al. Microarray applications in microbial ecology research. Microb Ecol. Aug. 2006;52(2):159-75. Epub Aug. 8, 2006.

Hazen, et al. Deep-sea oil plume enriches indigenous oil-degrading bacteria. Science. Oct. 8, 2010;330(6001):204-8. doi: 10.1126/science.1195979. Epub Aug. 24, 2010.

(56) References Cited

OTHER PUBLICATIONS

Karaman, et al. Comparisons of substitution, insertion and deletion probes for resequencing and mutational analysis using oligonucleotide microarrays, Nucleic Acids Research 2005, vol. 33, No. 3.

Klau, et al. Optimal robust non-unique probe selection using Integer Linear Programming. Bioinformatics. Aug. 4, 2004;20 Suppl 1:i186-93.

Loy, et al. Oligonucleotide microarray for 16S rRNA gene-based detection of all recognized lineages of sulfate-reducing prokaryotes in the environment. Appl Environ Microbiol. Oct. 2002;68(10):5064-81.

Mei, et al. Probe selection for high-density oligonucleotide arrays. Proc Natl Acad Sci U S A. Sep. 30, 2003;100(20):11237-42. Epub Sep. 19, 2003.

Palmer, et al. Rapid quantitative profiling of complex microbial populations. Nucleic Acids Res. Jan. 10, 2006;34(1):e5.

Rajilic-Stojanovic, et al. Development and application of the human intestinal tract chip, a phylogenetic microarray: analysis of universally conserved phylotypes in the abundant microbiota of young and elderly adults. Environ Microbiol. Jul. 2009;11(7):1736-51. doi: 10.1111/j.1462-2920.2009.01900.x. Epub Mar. 11, 2009.

Wagner, et al. Unravelling microbial communities with DNA-microarrays: challenges and future directions. Microb Ecol. Apr. 2007;53(3):498-506. Epub Mar. 8, 2007.

Wilson, et al. High-density microarray of small-subunit ribosomal DNA probes. Appl Environ Microbiol. May 2002;68(5):2535-41.

Wu, et al. Design of 16 S rRNA-based oligonnucleotide array using group-specific non-unique probes in large scale bacteria detection. Progress in Biochemistry and Biophysics. 2009; 36(8):1025-1034.

* cited by examiner

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Artificially Synthesized Primer

<400> SEQUENCE: 1
agrgtttgat cmtggctcag        20

<210> SEQ ID NO 2
<211> LENGTH: 19
<212> TYPE: DNA
<213> ORGANISM: Artificial Sequence
<220> FEATURE:
<223> OTHER INFORMATION: Artificially Synthesized Primer

<400> SEQUENCE: 2
ggttaccttg ttacgactt                                         19

<210> SEQ ID NO 3
<211> LENGTH: 20
<212> TYPE: DNA
<213> ORGANISM: Artificial Sequence
<220> FEATURE:
<223> OTHER INFORMATION: Artificially Synthesized Primer

<400> SEQUENCE: 3
cgactacctg gactgacact                                        20

<210> SEQ ID NO 4
<211> LENGTH: 20
<212> TYPE: DNA
<213> ORGANISM: Artificial Sequence
<220> FEATURE:
<223> OTHER INFORMATION: Artificially Synthesized Primer

<400> SEQUENCE: 4
caccggcagt ctccttagag                                        20

<210> SEQ ID NO 5
<211> LENGTH: 19
<212> TYPE: DNA
<213> ORGANISM: Artificial Sequence
<220> FEATURE:
<223> OTHER INFORMATION: Artificially Synthesized Primer

<400> SEQUENCE: 5
accaaggcta cgacgggta                                         19

<210> SEQ ID NO 6
<211> LENGTH: 19
<212> TYPE: DNA
<213> ORGANISM: Artificial Sequence
<220> FEATURE:
<223> OTHER INFORMATION: Artificially Synthesized Primer

<400> SEQUENCE: 6
acacaccgca tgtcaaacc                                         19

<210> SEQ ID NO 7
<211> LENGTH: 18
<212> TYPE: DNA
<213> ORGANISM: Artificial Sequence
<220> FEATURE:
<223> OTHER INFORMATION: Artificially Synthesized Primer

<400> SEQUENCE: 7
gggtggtaat gccsgatg                                          18

<210> SEQ ID NO 8
<211> LENGTH: 18
<212> TYPE: DNA
<213> ORGANISM: Artificial Sequence
<220> FEATURE:
<223> OTHER INFORMATION: Artificially Synthesized Primer

<400> SEQUENCE: 8
ccrccgttac accgggaa                                          18

<210> SEQ ID NO 9
<211> LENGTH: 20
<212> TYPE: DNA
<213> ORGANISM: Artificial Sequence

```
<220> FEATURE:
<223> OTHER INFORMATION: Artificially Synthesized Primer

<400> SEQUENCE: 9
caatggactc aagcctgatg                                          20

<210> SEQ ID NO 10
<211> LENGTH: 18
<212> TYPE: DNA
<213> ORGANISM: Artificial Sequence
<220> FEATURE:
<223> OTHER INFORMATION: Artificially Synthesized Primer

<400> SEQUENCE: 10
ctctagcctg cccgtttc                                            18

<210> SEQ ID NO 11
<211> LENGTH: 18
<212> TYPE: DNA
<213> ORGANISM: Artificial Sequence
<220> FEATURE:
<223> OTHER INFORMATION: Artificially Synthesized Primer

<400> SEQUENCE: 11
gagaggatga tcagccag                                            18

<210> SEQ ID NO 12
<211> LENGTH: 22
<212> TYPE: DNA
<213> ORGANISM: Artificial Sequence
<220> FEATURE:
<223> OTHER INFORMATION: Artificially Synthesized Primer

<400> SEQUENCE: 12
tacggytacc ttgttacgac tt                                       22

<210> SEQ ID NO 13
<211> LENGTH: 24
<212> TYPE: DNA
<213> ORGANISM: Artificial Sequence
<220> FEATURE:
<223> OTHER INFORMATION: Artificially Synthesized Primer

<400> SEQUENCE: 13
tccgtaggtg gctgttcaag tctg                                     24

<210> SEQ ID NO 14
<211> LENGTH: 24
<212> TYPE: DNA
<213> ORGANISM: Artificial Sequence
<220> FEATURE:
<223> OTHER INFORMATION: Artificially Synthesized Primer

<400> SEQUENCE: 14
gctttcgtcc ctcagtgtca gttg                                     24

<210> SEQ ID NO 15
<211> LENGTH: 24
<212> TYPE: DNA
<213> ORGANISM: Artificial Sequence
<220> FEATURE:
<223> OTHER INFORMATION: Artificially Synthesized Primer

<400> SEQUENCE: 15
tgtcgtgaga tgttgggtta agtc                                     24
```

```
<210> SEQ ID NO 16
<211> LENGTH: 24
<212> TYPE: DNA
<213> ORGANISM: Artificial Sequence
<220> FEATURE:
<223> OTHER INFORMATION: Artificially Synthesized Primer

<400> SEQUENCE: 16
tgagccgtgg tttaagagat tagc                                          24

<210> SEQ ID NO 17
<211> LENGTH: 20
<212> TYPE: DNA
<213> ORGANISM: Artificial Sequence
<220> FEATURE:
<223> OTHER INFORMATION: Artificially Synthesized Primer

<400> SEQUENCE: 17
gcctcacgcc ataagattag                                               20

<210> SEQ ID NO 18
<211> LENGTH: 22
<212> TYPE: DNA
<213> ORGANISM: Artificial Sequence
<220> FEATURE:
<223> OTHER INFORMATION: Artificially Synthesized Primer

<400> SEQUENCE: 18
gtgctttctt ctgtaagtaa cg                                            22

<210> SEQ ID NO 19
<211> LENGTH: 15
<212> TYPE: DNA
<213> ORGANISM: Artificial Sequence
<220> FEATURE:
<223> OTHER INFORMATION: Artificially Synthesized Primer

<400> SEQUENCE: 19
tcgaaaagcg tgggg                                                    15

<210> SEQ ID NO 20
<211> LENGTH: 15
<212> TYPE: DNA
<213> ORGANISM: Artificial Sequence
<220> FEATURE:
<223> OTHER INFORMATION: Artificially Synthesized Primer

<400> SEQUENCE: 20
cttcctcccc cgttc                                                    15

<210> SEQ ID NO 21
<211> LENGTH: 16
<212> TYPE: DNA
<213> ORGANISM: Artificial Sequence
<220> FEATURE:
<223> OTHER INFORMATION: Artificially Synthesized Primer

<400> SEQUENCE: 21
gaaactgccc agacac                                                   16

<210> SEQ ID NO 22
<211> LENGTH: 16
<212> TYPE: DNA
<213> ORGANISM: Artificial Sequence
<220> FEATURE:
<223> OTHER INFORMATION: Artificially Synthesized Primer
```

```
<400> SEQUENCE: 22
agtaacgttc gcacag                                                    16

<210> SEQ ID NO 23
<211> LENGTH: 18
<212> TYPE: DNA
<213> ORGANISM: Artificial Sequence
<220> FEATURE:
<223> OTHER INFORMATION: Artificially Synthesized Primer

<400> SEQUENCE: 23
ggatgacact tttcggag                                                  18

<210> SEQ ID NO 24
<211> LENGTH: 18
<212> TYPE: DNA
<213> ORGANISM: Artificial Sequence
<220> FEATURE:
<223> OTHER INFORMATION: Artificially Synthesized Primer

<400> SEQUENCE: 24
aattccatct gcctctcc                                                  18

<210> SEQ ID NO 25
<211> LENGTH: 17
<212> TYPE: DNA
<213> ORGANISM: Artificial Sequence
<220> FEATURE:
<223> OTHER INFORMATION: Artificially Synthesized Primer

<400> SEQUENCE: 25
ggcggcgcgt tttaagc                                                   17

<210> SEQ ID NO 26
<211> LENGTH: 17
<212> TYPE: DNA
<213> ORGANISM: Artificial Sequence
<220> FEATURE:
<223> OTHER INFORMATION: Artificially Synthesized Primer

<400> SEQUENCE: 26
actcgggtgg tgtgacg                                                   17

<210> SEQ ID NO 27
<211> LENGTH: 19
<212> TYPE: DNA
<213> ORGANISM: Artificial Sequence
<220> FEATURE:
<223> OTHER INFORMATION: Artificially Synthesized Primer

<400> SEQUENCE: 27
aytgggcgta aagagttgc                                                 19

<210> SEQ ID NO 28
<211> LENGTH: 22
<212> TYPE: DNA
<213> ORGANISM: Artificial Sequence
<220> FEATURE:
<223> OTHER INFORMATION: Artificially Synthesized Primer

<400> SEQUENCE: 28
tacggytacc ttgttacgac tt                                             22
```

ARRAY FOR DETECTING MICROBES

CROSS-REFERENCE TO RELATED APPLICATIONS

This application is a continuation of, and claims the benefit of priority to, PCT Application No. PCT/US2007/024720, filed Nov. 29, 2007, which was written in English, published in English as WO/2008/130394 and designated the United States of America, which claims priority under 35 U.S.C. §119(e) to U.S. Provisional Application No. 60/861,834 filed Nov. 30, 2006, both of which are hereby incorporated by reference in their entirety.

STATEMENT REGARDING FEDERALLY SPONSORED R&D

This invention was made with Government support under Grant No. DE-AC03-76SF00098 from the Department of Homeland Security and Contract No. DE-AC0-05CH11231 from the Department of Energy.

REFERENCE TO SEQUENCE LISTING

The present application is being filed along with a Sequence Listing in electronic format. The Sequence Listing is provided as a file entitled LBNL026C1.TXT, created May 28, 2009, which is 5.51 KB in size. The information in the electronic format of the Sequence Listing is incorporated herein by reference in its entirety.

BACKGROUND OF THE INVENTION

1. Field of the Invention

The present embodiments relate to an array system for detecting and identifying biomolecules and organisms. More specifically, the present embodiments relate to an array system comprising a microarray configured to simultaneously detect a plurality of organisms in a sample at a high confidence level.

2. Description of the Related Art

In the fields of molecular biology and biochemistry, biopolymers such as nucleic acids and proteins from organisms are identified and/or fractionated in order to search for useful genes, diagnose diseases or identify organisms. A hybridization reaction is frequently used as a pretreatment for such process, where a target molecule in a sample is hybridized with a nucleic acid or a protein having a known sequence. For this purpose, microarrays, or DNA chips, are used on which probes such as DNAs, RNAs or proteins with known sequences are immobilized at predetermined positions.

A DNA microarray (also commonly known as gene or genome chip, DNA chip, or gene array) is a collection of microscopic DNA spots attached to a solid surface, such as glass, plastic or silicon chip forming an array. The affixed DNA segments are known as probes (although some sources will use different nomenclature), thousands of which can be used in a single DNA microarray. Measuring gene expression using microarrays is relevant to many areas of biology and medicine, such as studying treatments, disease, and developmental stages. For example, microarrays can be used to identify disease genes by comparing gene expression in diseased and normal cells.

Molecular approaches designed to describe organism diversity routinely rely upon classifying heterogeneous nucleic acids amplified by universal 16S RNA gene PCR (polymerase chain reaction). The resulting mixed amplicons can be quickly, but coarsely, typed into anonymous groups using T-/RFLP (Terminal Restriction Fragment Length Polymorphism), SSCP (single-strand conformation polymorphism) or T/DGGE (temperature/denaturing gradient gel electrophoresis). These groups may be classified through sequencing, but this requires additional labor to physically isolate each 16S RNA type, does not scale well for large comparative studies such as environmental monitoring, and is only suitable for low complexity environments. Also, the number of clones that would be required to adequately catalogue the majority of taxa in a sample is too large to be efficiently or economically handled. As such, an improved array and method is needed to efficiently analyze a plurality of organisms without the disadvantages of the above technologies.

SUMMARY OF THE INVENTION

Some embodiments relate to an array system including a microarray configured to simultaneously detect a plurality of organisms in a sample, wherein the microarray comprises fragments of 16s RNA unique to each organism and variants of said fragments comprising at least 1 nucleotide mismatch, wherein the level of confidence of species-specific detection derived from fragment matches is about 90% or higher.

In one aspect, the plurality of organisms comprise bacteria or archaea.

In another aspect, the fragments of 16s RNA are clustered and aligned into groups of similar sequence such that detection of an organism based on at least 1 fragment matches is possible.

In yet another aspect, the level of confidence of species-specific detection derived from fragment matches is about 95% or higher.

In still another aspect, the level of confidence of species-specific detection derived from fragment matches is about 98% or higher.

In some embodiments, the majority of fragments of 16s RNA unique to each organism have a corresponding variant fragment comprising at least 1 nucleotide mismatch.

In some aspects, every fragment of 16s RNA unique to each organism has a corresponding variant fragment comprising at least 1 nucleotide mismatch.

In other aspects, the fragments are about 25 nucleotides long.

In some aspects, the sample is an environmental sample.

In other aspects, the environmental sample comprises at least one of soil, water or atmosphere.

In yet other aspects, the sample is a clinical sample.

In still other aspects, the clinical sample comprises at least one of tissue, skin, bodily fluid or blood.

Some embodiments relate to a method of detecting an organism including applying a sample comprising a plurality of organisms to the array system which includes a microarray that comprises fragments of 16s RNA unique to each organism and variants of said fragments comprising at least 1 nucleotide mismatch, wherein the level of confidence of species-specific detection derived from fragment matches is about 90% or higher; and identifying organisms in the sample.

In some aspects, the plurality of organisms comprise bacteria or archaea.

In other aspects, the majority of fragments of 16s RNA unique to each organism have a corresponding variant fragment comprising at least 1 nucleotide mismatch.

In still other aspects, every fragment of 16s RNA unique to each organism has a corresponding variant fragment comprising at least 1 nucleotide mismatch.

In yet other aspects, the fragments are about 25 nucleotides long.

In some aspects, the organism to be detected is the most metabolically active organism in the sample.

Some embodiments relate to a method of fabricating an array system including identifying 16s RNA sequences corresponding to a plurality of organisms of interest; selecting fragments of 16s RNA unique to each organism; creating variant RNA fragments corresponding to the fragments of 16s RNA unique to each organism which comprise at least 1 nucleotide mismatch; and fabricating said array system.

In some aspects, the plurality of organisms comprise bacteria or archaea.

In other aspects, the majority of fragments of 16s RNA unique to each organism have a corresponding variant fragment comprising at least 1 nucleotide mismatch.

In still other aspects, every fragment of 16s RNA unique to each organism has a corresponding variant fragment comprising at least 1 nucleotide mismatch.

In yet other aspects, the fragments are about 25 nucleotides long.

DETAILED DESCRIPTION

Figure 1:
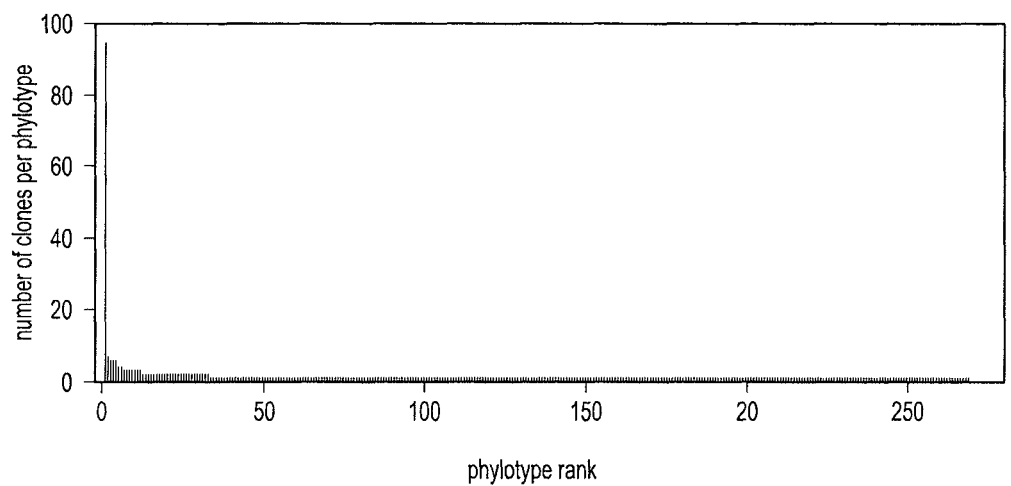
FIG. 1 is a bar graph showing rank-abundance curve of phylotypes within the urban aerosol clone library obtained from San Antonio calendar week 29. Phylotypes were determined by clustering at 99% homology using nearest neighbor joining.
Figure 2:
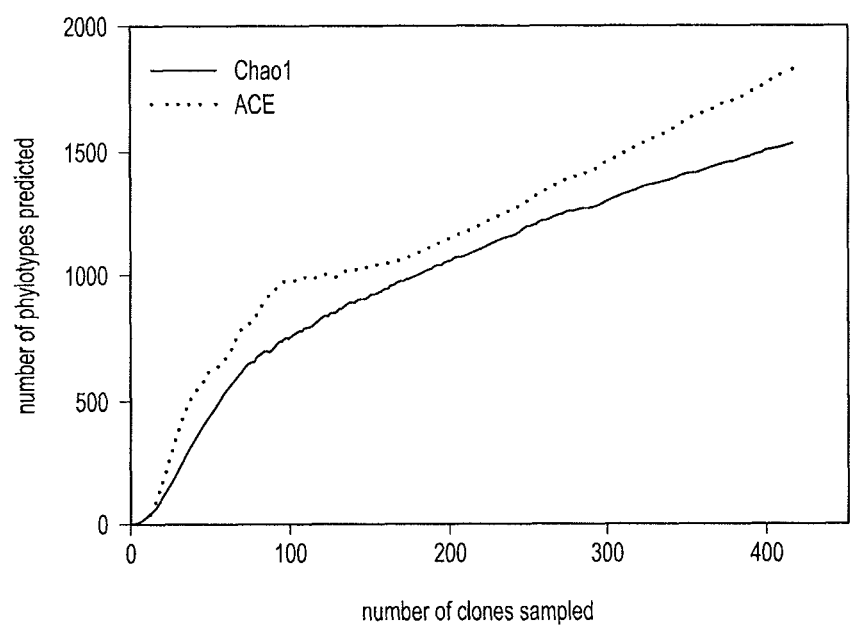
FIG. 2 is a line graph showing that Chao1 and ACE richness estimators are non-asymptotic, indicating an under-estimation of predicted richness based on numbers of clones sequenced.

The present embodiments are related to an array system for detecting and identifying biomolecules and organisms. More specifically, the present embodiments relate to an array system comprising a microarray configured to simultaneously detect a plurality of organisms in a sample at a high confidence level.

In some embodiments, the array system uses multiple probes for increasing confidence of identification of a particular organism using a 16S rRNA gene targeted high density microarray. The use of multiple probes can greatly increase the confidence level of a match to a particular organism. Also, in some embodiments, mismatch control probes corresponding to each perfect match probe can be used to further increase confidence of sequence-specific hybridization of a target to a probe. Probes with one or more mismatch can be used to indicate non-specific binding and a possible non-match. This has the advantage of reducing false positive results due to non-specific hybridization, which is a significant problem with many current microarrays.

Some embodiments of the invention relate to a method of using an array to simultaneously identify multiple prokaryotic taxa with a relatively high confidence. A taxa is an individual microbial species or group of highly related species that share an average of about 97% 16S rRNA gene sequence identity. The array system of the current embodiments may use multiple confirmatory probes, each with from about 1 to about 20 corresponding mismatch control probes to target the most unique regions within a 16S rRNA gene for about 9000 taxa. Preferably, each confirmatory probe has from about 1 to about 10 corresponding mismatch probes. More preferably, each confirmatory probe has from about 1 to about 5 corresponding mismatch probes. The aforementioned about 9000 taxa represent a majority of the taxa that are currently known through 16S rRNA clone sequence libraries. In some embodiments, multiple targets can be assayed through a high-density oligonucleotide array. The sum of all target hybridizations is used to identify specific prokaryotic taxa. The result is a much more efficient and less time consuming way of identifying unknown organisms that in addition to providing results that could not previously be achieved, can also provide results in hours that other methods would require days to achieve.

In some embodiments, the array system of the present embodiments can be fabricated using 16s rRNA sequences as follows. From about 1 to about 500 short probes can be designed for each taxonomic group. In some embodiments, the probes can be proteins, antibodies, tissue samples or oligonucleotide fragments. In certain examples, oligonucleotide fragments are used as probes. In some embodiments, from about 1 to about 500 short oligonucleotide probes, preferably from about 2 to about 200 short oligonucleotide probes, more preferably from about 5 to about 150 short oligonucleotide probes, even more preferably from about 8 to about 100 short oligonucleotide probes can be designed for each taxonomic grouping, allowing for the failure of one or more probes. In one example, at least about 11 short oligonucleotide probes are used for each taxonomic group. The oligonucleotide probes can each be from about 5 bp to about 100 bp, preferably from about 10 bp to about 50 bp, more preferably from about 15 bp to about 35 bp, even more preferably from about 20 bp to about 30 bp. In some embodiments, the probes may be 5-mers, 6-mers, 7-mers, 8-mers, 9-mers, 10-mers, 11-mers, 12-mers, 13-mers, 14-mers, 15-mers, 16-mers, 17-mers, 18-mers, 19-mers, 20-mers, 21-mers, 22-mers, 23-mers, 24-mers, 25-mers, 26-mers, 27-mers, 28-mers, 29-mers, 30-mers, 31-mers, 32-mers, 33-mers, 34-mers, 35-mers, 36-mers, 37-mers, 38-mers, 39-mers, 40-mers, 41-mers, 42-mers, 43-mers, 44-mers, 45-mers, 46-mers, 47-mers, 48-mers, 49-mers, 50-mers, 51-mers, 52-mers, 53-mers, 54-mers, 55-mers, 56-mers, 57-mers, 58-mers, 59-mers, 60-mers, 61-mers, 62-mers, 63-mers, 64-mers, 65-mers, 66-mers, 67-mers, 68-mers, 69-mers, 70-mers, 71-mers, 72-mers, 73-mers, 74-mers, 75-mers, 76-mers, 77-mers, 78-mers, 79-mers, 80-mers, 81-mers, 82-mers, 83-mers, 84-mers, 85-mers, 86-mers, 87-mers, 88-mers, 89-mers, 90-mers, 91-mers, 92-mers, 93-mers, 94-mers, 95-mers, 96-mers, 97-mers, 98-mers, 99-mers, 100-mers or combinations thereof.

Non-specific cross hybridization can be an issue when an abundant 16S rRNA gene shares sufficient sequence similarity to non-targeted probes, such that a weak but detectable signal is obtained. The use of sets of perfect match and mismatch probes (PM-MM) effectively minimizes the influence of cross-hybridization. In certain embodiments, each perfect match probe (PM) has one corresponding mismatch probe (MM) to form a pair that are useful for analyzing a particular 16S rRNA sequence. In other embodiments, each PM has more than one corresponding MM. Additionally, different PMs can have different numbers of corresponding MM probes. In some embodiments, each PM has from about 1 to about 20 MM, preferably, each PM has from about 1 to about 10 MM and more preferably, each PM has from about 1 to about 5 MM.

Any of the nucleotide bases can be replaced in the MM probe to result in a probe having a mismatch. In one example, the central nucleotide base sequence can be replaced with any of the three non-matching bases. In other examples, more than one nucleotide base in the MM is replaced with a non-matching base. In some examples, 10 nucleotides are replaced in the MM, in other examples, 5 nucleotides are replaced in the MM, in yet other examples 3 nucleotides are replaced in the MM, and in still other examples, 2 nucleotides are replaced in the MM. This is done so that the increased hybridization intensity signal of the PM over the one or more MM indicates a sequence-specific positive hybridization. By requiring multiple PM-MM probes to have a confirmation interaction, the chance that the hybridization signal is due to a predicted target sequence is substantially increased.

In other embodiments, the 16S rRNA gene sequences can be grouped into distinct taxa such that a set of the short oligonucleotide probes that are specific to the taxon can be chosen. In some examples, the 16s rRNA gene sequences grouped into distinct taxa are from about 100 bp to about 1000 bp, preferably the gene sequences are from about 400 bp to about 900 bp, more preferably from about 500 bp to about 800 bp. The resulting about 9000 taxa represented on the array, each containing from about 1% to about 5% sequence divergence, preferably about 3% sequence divergence, can represent substantially all demarcated bacterial and archaeal orders.

In some embodiments, for a majority of the taxa represented on the array, probes can be designed from regions of gene sequences that have only been identified within a given taxon. In other embodiments, some taxa have no probe-level sequence that can be identified that is not shared with other groups of 16S rRNA gene sequences. For these taxonomic groupings, a set of from about 1 to about 500 short oligonucleotide probes, preferably from about 2 to about 200 short oligonucleotide probes, more preferably from about 5 to about 150 short oligonucleotide probes, even more preferably from about 8 to about 100 short oligonucleotide probes can be designed to a combination of regions on the 16S rRNA gene that taken together as a whole do not exist in any other taxa. For the remaining taxa, a set of probes can be selected to minimize the number of putative cross-reactive taxa. For all three probe set groupings, the advantage of the hybridization approach is that multiple taxa can be identified simultaneously by targeting unique regions or combinations of sequence.

In some embodiments, oligonucleotide probes can then be selected to obtain an effective set of probes capable of correctly identifying the sample of interest. In certain embodiments, the probes are chosen based on various taxonomic organizations useful in the identification of particular sets of organisms.

In some embodiments, the chosen oligonucleotide probes can then be synthesized by any available method in the art. Some examples of suitable methods include printing with fine-pointed pins onto glass slides, photolithography using pre-made masks, photolithography using dynamic micromirror devices, ink-jet printing or electrochemistry. In one example, a photolithographic method can be used to directly synthesize the chosen oligonucleotide probes onto a surface. Suitable examples for the surface include glass, plastic, silicon and any other surface available in the art. In certain examples, the oligonucleotide probes can be synthesized on a glass surface at an approximate density of from about 1,000 probes per $\mu m^2$ to about 100,000 probes per $\mu m^2$, preferably from about 2000 probes per $\mu m^2$ to about 50,000 probes per $\mu m^2$, more preferably from about 5000 probes per $\mu m^2$ to about 20,000 probes per $\mu m^2$. In one example, the density of the probes is about 10,000 probes per $\mu m^2$. The array can then be arranged in any configuration, such as, for example, a square grid of rows and columns. Some areas of the array can be oligonucleotide 16S rDNA PM or MM probes, and others can be used for image orientation, normalization controls or other analyses. In some embodiments, materials for fabricating the array can be obtained from Affymetrix, GE Healthcare (Little Chalfont, Buckinghamshire, United Kingdom) or Agilent Technologies (Palo Alto, Calif.)

In some embodiments, the array system is configured to have controls. Some examples of such controls include 1) probes that target amplicons of prokaryotic metabolic genes spiked into the 16S rDNA amplicon mix in defined quantities just prior to fragmentation and 2) probes complimentary to a pre-labeled oligonucleotide added into the hybridization mix. The first control collectively tests the fragmentation, biotinylation, hybridization, staining and scanning efficiency of the array system. It also allows the overall fluorescent intensity to be normalized across all the arrays in an experiment. The second control directly assays the hybridization, staining and scanning of the array system. However, the array system of the present embodiments is not limited to these particular examples of possible controls.

The accuracy of the array of some embodiments has been validated by comparing the results of some arrays with 16S rRNA gene sequences from approximately 700 clones in each of 3 samples. A specific taxa is identified as being present in a sample if a majority (from about 70% to about 100%, preferably from about 80% to about 100% and more preferably from about 90% to about 100%) of the probes on the array have a hybridization signal about 100 times, 200 times, 300 times, 400 times or 500 times greater than that of the background and the perfect match probe has a significantly greater hybridization signal than its one or more partner mismatch control probe or probes. This ensures a higher probability of a sequence specific hybridization to the probe. In some embodiments, the use of multiple probes, each independently indicating that the target sequence of the taxonomic group being identified is present, increases the probability of a correct identification of the organism of interest.

Biomolecules, such proteins, DNA, RNA, DNA from amplified products and native rRNA from the 16S rRNA gene, for example can be probed by the array of the present embodiments. In some embodiments, probes are designed to be antisense to the native rRNA so that directly labeled rRNA from samples can be placed directly on the array to identify a majority of the actively metabolizing organisms in a sample with no bias from PCR amplification. Actively metabolizing organisms have significantly higher numbers of ribosomes used for the production of proteins, therefore, in some embodiments, the capacity to make proteins at a particular point in time of a certain organism can be measured. This is not possible in systems where only the 16S rRNA gene DNA is measured which encodes only the potential to make proteins and is the same whether an organism is actively metabolizing or quiescent or dead. In this way, the array system of the present embodiments can directly identify the metabolizing organisms within diverse communities.

In some embodiments, the array system is able to measure the microbial diversity of complex communities without PCR amplification, and consequently, without all of the inherent biases associated with PCR amplification. Actively metabolizing cells typically have about 20,000 or more ribosomal copies within their cell for protein assembly compared to quiescent or dead cells that have few. In some embodiments, rRNA can be purified directly from environmental samples and processed with no amplification step, thereby avoiding any of the biases caused by the preferential amplification of some sequences over others. Thus, in some embodiments the signal from the array system can reflect the true number of rRNA molecules that are present in the samples, which can be expressed as the number of cells multiplied by the number of rRNA copies within each cell. The number of cells in a sample can then be inferred by several different methods, such as, for example, quantitative real-time PCR, or FISH (fluorescence in situ hybridization.) Then the average number of ribosomes within each cell may be calculated.

In some embodiments, the samples used can be environmental samples from any environmental source, for example, naturally occurring or artificial atmosphere, water systems, soil or any other sample of interest. In some embodiments, the environmental samples may be obtained from, for example, atmospheric pathogen collection systems, sub-surface sediments, groundwater, ancient water deep within the ground, plant root-soil interface of grassland, coastal water and sewage treatment plants. Because of the ability of the array system to simultaneously test for such a broad range of organisms based on almost all known 16s rRNA gene sequences, the array system of the present embodiments can be used in any environment, which also distinguishes it from other array systems which generally must be targeted to specific environments.

In other embodiments, the sample used with the array system can be any kind of clinical or medical sample. For example, samples from blood, the lungs or the gut of mammals may be assayed using the array system. Also, the array system of the present embodiments can be used to identify an infection in the blood of an animal. The array system of the present embodiments can also be used to assay medical samples that are directly or indirectly exposed to the outside of the body, such as the lungs, ear, nose, throat, the entirety of the digestive system or the skin of an animal. Hospitals currently lack the resources to identify the complex microbial communities that reside in these areas.

Another advantage of the present embodiments is that simultaneous detection of a majority of currently known organisms is possible with one sample. This allows for much more efficient study and determination of particular organisms within a particular sample. Current microarrays do not have this capability. Also, with the array system of the present embodiments, simultaneous detection of the top metabolizing organisms within a sample can be determined without bias from PCR amplification, greatly increasing the efficiency and accuracy of the detection process.

Some embodiments relate to methods of detecting an organism in a sample using the described array system. These methods include contacting a sample with one organism or a plurality of organisms to the array system of the present embodiments and detecting the organism or organisms. In some embodiments, the organism or organisms to be detected are bacteria or archaea. In some embodiments, the organism or organisms to be detected are the most metabolically active organism or organisms in the sample.

Some embodiments relate to a method of fabricating an array system including identifying 16s RNA sequences corresponding to a plurality of organisms of interest, selecting fragments of 16s RNA unique to each organism and creating variant RNA fragments corresponding to the fragments of 16s RNA unique to each organism which comprise at least 1 nucleotide mismatch and then fabricating the array system.

The following examples are provided for illustrative purposes only, and are in no way intended to limit the scope of the present invention.

EXAMPLE 1

An array system was fabricated using 16s rRNA sequences taken from a plurality of bacterial species. A minimum of 11 different, short oligonucleotide probes were designed for each taxonomic grouping, allowing one or more probes to not bind, but still give a positive signal in the assay. Non-specific cross hybridization is an issue when an abundant 16S rRNA gene shares sufficient sequence similarity to non-targeted probes, such that a weak but detectable signal is obtained. The use of a perfect match-mismatch (PM-MM) probe pair effectively minimized the influence of cross-hybridization. In this technique, the central nucleotide is replaced with any of the three non-matching bases so that the increased hybridization intensity signal of the PM over the paired MM indicates a sequence-specific, positive hybridization. By requiring multiple PM-MM probe-pairs to have a positive interaction, the chance that the hybridization signal is due to a predicted target sequence is substantially increased.

The known 16S rRNA gene sequences larger than 600 bp were grouped into distinct taxa such that a set of at least 11 probes that were specific to each taxon could be selected. The resulting 8,935 taxa (8,741 of which are represented on the array), each containing approximately 3% sequence divergence, represented all 121 demarcated bacterial and archacal orders. For a majority of the taxa represented on the array (5,737, 65%), probes were designed from regions of 16S rRNA gene sequences that have only been identified within a given taxon. For 1,198 taxa (14%) no probe-level sequence could be identified that was not shared with other groups of 16S rRNA gene sequences, although the gene sequence as a whole was distinctive. For these taxonomic groupings, a set of at least 11 probes was designed to a combination of regions on the 16S rRNA gene that taken together as a whole did not exist in any other taxa. For the remaining 1,806 taxa (21%), a set of probes were selected to minimize the number of putative cross-reactive taxa. Although more than half of the probes in this group have a hybridization potential to one outside sequence, this sequence was typically from a phylogenetically similar taxon. For all three probe set groupings, the advantage of the hybridization approach is that multiple taxa can be identified simultaneously by targeting unique regions or combinations of sequence.

EXAMPLE 2

An array system was fabricated according to the following protocol. 16S rDNA sequences (*Escherichia coli* base pair positions 47 to 1473) were obtained from over 30,000 16S rDNA sequences that were at least 600 nucleotides in length in the 15 Mar. 2002 release of the 16S rDNA database, "Greengenes." This region was selected because it is bounded on both ends by universally conserved segments that can be used as PCR priming sites to amplify bacterial or archaeal genomic material using only 2 to 4 primers. Putative chimeric sequences were filtered from the data set using computer software preventing them from being misconstrued as novel organisms. The filtered sequences are considered to be the set of putative 16S rDNA amplicons. Sequences were clustered to enable each sequence of a cluster to be complementary to a set of perfectly matching (PM) probes. Putative amplicons were placed in the same cluster as a result of common 17-mers found in the sequence.

The resulting 8,988 clusters, each containing approximately 3% sequence divergence, were considered operational taxonomic units (OTUs) representing all 121 demarcated prokaryotic orders. The taxonomic family of each OTU was assigned according to the placement of its member organisms in Bergey's Taxonomic Outline. The taxonomic outline as maintained by Philip Hugenholtz was consulted for phylogenetic classes containing uncultured environmental organisms or unclassified families belonging to named higher taxa. The OTUs comprising each family were clustered into sub-families by transitive sequence identity. Altogether, 842 sub-families were found. The taxonomic position of each OTU as well as the accompanying NCBI accession numbers of the sequences composing each OTU are recorded and publicly available.

The objective of the probe selection strategy was to obtain an effective set of probes capable of correctly categorizing mixed amplicons into their proper OTU. For each OTU, a set of 11 or more specific 25-mers (probes) were sought that were prevalent in members of a given OTU but were dissimilar from sequences outside the given OTU. In the first step of probe selection for a particular OTU, each of the sequences in the OTU was separated into overlapping 25-mers, the potential targets. Then each potential target was matched to as many sequences of the OTU as possible. First, a text pattern was used for a search to match potential targets and sequences, however, since partial gene sequences were included in the reference set additional methods were performed. Therefore, the multiple sequence alignment provided by Greengenes was used to provide a discrete measurement of group size at each potential probe site. For example, if an OTU containing seven sequences possessed a probe site where one member was missing data, then the site-specific OTU size was only six.

In ranking the possible targets, those having data for all members of that OTU were preferred over those found only in a fraction of the OTU members. In the second step, a subset of the prevalent targets was selected and reverse complimented into probe orientation, avoiding those capable of mis-hybridization to an unintended amplicon. Probes presumed to have the capacity to mis-hybridize were those 25-mers that contained a central 17-mer matching sequences in more than one OTU. Thus, probes that were unique to an OTU solely due to a distinctive base in one of the outer four bases were avoided. Also, probes with mis-hybridization potential to sequences having a common tree node near the root were favored over those with a common node near the terminal branch.

Probes complementary to target sequences that were selected for fabrication were termed perfectly matching (PM) probes. As each PM probe was chosen, it was paired with a control 25-mer (mismatching probe, MM), identical in all positions except the thirteenth base. The MM probe did not contain a central 17-mer complimentary to sequences in any OTU. The probe complementing the target (PM) and MM probes constitute a probe pair analyzed together.

The chosen oligonucleotides were synthesized by a photolithographic method at Affymetrix Inc. (Santa Clara, Calif., USA) directly onto a 1.28 cm by 1.28 cm glass surface at an approximate density of 10,000 probes per $\mu m^2$. Each unique probe sequence on the array had a copy number of roughly $3.2 \times 10^6$ (personal communication, Affymetrix). The entire array of 506,944 features was arranged as a square grid of 712 rows and columns. Of these features, 297,851 were oligonucleotide 16S rDNA PM or MM probes, and the remaining were used for image orientation, normalization controls or other unrelated analyses. Each DNA chip had two kinds of controls on it: 1) probes that target amplicons of prokaryotic metabolic genes spiked into the 16S rDNA amplicon mix in defined quantities just prior to fragmentation and 2) probes complimentary to a pre-labeled oligonucleotide added into the hybridization mix. The first control collectively tested the fragmentation, biotinylation, hybridization, staining and scanning efficiency. It also allowed the overall fluorescent intensity to be normalized across all the arrays in an experiment. The second control directly assayed the hybridization, staining and scanning.

EXAMPLE 3

A study was done on diverse and dynamic bacterial population in urban aerosols utilizing an array system of certain embodiments. Air samples were collected using an air filtration collection system under vacuum located within six EPA air quality network sites in both San Antonio and Austin, Tex. Approximately 10 liters of air per minute were collected in a polyethylene terephthalate (Celanex), 1.0 µm filter (Hoechst Calanese). Samples were collected daily over a 24 h period. Sample filters were washed in 10 mL buffer (0.1 M Sodium Phosphate, 10 mM EDTA, pH 7.4, 0.01% Tween-20), and the suspension was stored frozen until extracted. Samples were collected from 4 May to 29 Aug. 2003.

Sample dates were divided according to a 52-week calendar year starting Jan. 1, 2003, with each Monday to Sunday cycle constituting a full week. Samples from four randomly chosen days within each sample week were extracted. Each date chosen for extraction consisted of 0.6 mL filter wash from each of the six sampling sites for that city (San Antonio or Austin) combined into a "day pool" before extraction. In total, for each week, 24 filters were sampled.

The "day pools" were centrifuged at 16,000×g for 25 min and the pellets were resuspended in 400 µL sodium phosphate buffer (100 mM, pH 8). The resuspended pellets were transferred into 2 mL silica bead lysis tubes containing 0.9 g of silica/zirconia lysis bead mix (0.3 g of 0.5 mm zirconia/silica beads and 0.6 g of 0.1 mm zirconia/silica beads). For each lysis tube, 300 µL buffered sodium dodecyl sulfate (SDS) (100 mM sodium chloride, 500 mM Tris pH 8, 10% [w/v] SDS), and 300 µL phenol:chloroform:isoamyl alcohol (25:24:1) were added. Lysis tubes were inverted and flicked three times to mix buffers before bead mill homogenization with a Bio101 Fast Prep 120 machine (Qbiogene, Carlsbad, Calif.) at 6.5 m s$^{-1}$ for 45 s. Following centrifugation at 16,000×g for 5 min, the aqueous supernatant was removed to a new 2 mL tube and kept at −20° C. for 1 hour to overnight. An equal volume of chloroform was added to the thawed supernatant prior to vortexing for 5 s and centrifugation at 16,000×g for 3 min. The supernatant was then combined with two volumes of a binding buffer "Solution 3" (UltraClean Soil DNA kit, MoBio Laboratories, Solana Beach, Calif.). Genomic DNA from the mixture was isolated on a MoBio spin column, washed with "Solution 4" and eluted in 60 µL of 1× Tris-EDTA according to the manufacturer's instructions. The DNA was further purified by passage through a Sephacryl S-200 HR spin column (Amersham, Piscataway, N.J., USA) and stored at 4° C. prior to PCR amplification. DNA was quantified using a PicoGreen fluorescence assay according to the manufacturer's recommended protocol (Invitrogen, Carlsbad, Calif.).

The 16S rRNA gene was amplified from the DNA extract using universal primers 27F.1, (5' AGRGTTTGATCMTG-GCTCAG) (SEQ ID NO: 1) and 1492R, (5' GGTTACCT-TGTTACGACTT) (SEQ ID NO: 2). Each PCR reaction mix contained 1× Ex Taq buffer (Takara Bio Inc, Japan), 0.8 mM dNTP mixture, 0.02 U/μL Ex Taq polymerase, 0.4 mg/mL bovine serum albumin (BSA), and 1.0 μM each primer. PCR conditions were 1 cycle of 3 min at 95° C., followed by 35 cycles of 30 see at 95° C., 30 sec at 53° C., and 1 min at 72° C., and finishing with 7 min incubation at 72° C. When the total mass of PCR product for a sample week reached 2 μg (by gel quantification), all PCR reactions for that week were pooled and concentrated to a volume less than 40 μL with a Micron YM100 spin filter (Millipore, Billerica, Mass.) for microarray analysis.

The pooled PCR product was spiked with known concentrations of synthetic 16S rRNA gene fragments and non-16S rRNA gene fragments according to Table S1. This mix was fragmented using DNAse I (0.02 U/μg DNA, Invitrogen, CA) and One-Phor-All buffer (Amersham, N.J.) per Affymetrix's protocol, with incubation at 25° C. for 10 min., followed by enzyme denaturation at 98° C. for 10 min. Biotin labeling was performed using an Enzo® BioArray™ Terminal Labeling Kit (Enzo Life Sciences Inc., Farmingdale, N.Y.) per the manufacturer's directions. The labeled DNA was then denatured (99° C. for 5 min) and hybridized to the DNA microarray at 48° C. overnight (>16 hr). The microarrays were washed and stained per the Affymetrix protocol.

The array was scanned using a GeneArray Scanner (Affymetrix, Santa Clara, Calif., USA). The scan was recorded as a pixel image and analyzed using standard Affymetrix software (Microarray Analysis Suite, version 5.1) that reduced the data to an individual signal value for each probe. Background probes were identified as those producing intensities in the lowest 2% of all intensities. The average intensity of the background probes was subtracted from the fluorescence intensity of all probes. The noise value (N) was the variation in pixel intensity signals observed by the scanner as it read the array surface. The standard deviation of the pixel intensities within each of the identified background cells was divided by the square root of the number of pixels comprising that cell. The average of the resulting quotients was used for N in the calculations described below.

Probe pairs scored as positive were those that met two criteria: (i) the intensity of fluorescence from the perfectly matched probe (PM) was greater than 1.3 times the intensity from the mismatched control (MM), and (ii) the difference in intensity, PM minus MM, was at least 130 times greater than the squared noise value (>130 $N^2$). These two criteria were chosen empirically to provide stringency while maintaining sensitivity to the amplicons known to be present from sequencing results of cloning the San Antonio week 29 sample. The positive fraction (PosFrac) was calculated for each probe set as the number of positive probe pairs divided by the total number of probe pairs in a probe set. A taxon was considered present in the sample when over 92% of its assigned probe pairs for its corresponding probe set were positive (PosFrac>0.92). This was determined based on empirical data from clone library analyses. Hybridization intensity (hereafter referred to as intensity) was calculated in arbitrary units (a.u.) for each probe set as the trimmed average (maximum and minimum values removed before averaging) of the PM minus MM intensity differences across the probe pairs in a given probe set. All intensities <1 were shifted to 1 to avoid errors in subsequent logarithmic transformations. When summarizing chip results to the sub-family, the probe set producing the highest intensity was used.

To compare the diversity of bacteria detected with microarrays to a known standard, one sample week was chosen for cloning and sequencing and for replicate microarray analysis. One large pool of SSU amplicons (96 reactions, 50 μL/reaction) from San Antonio week 29 was made. One milliliter of the pooled PCR product was gel purified and 768 clones were sequenced at the DOE Joint Genome Institute (Walnut Creek, Calif.) by standard methods. An aliquot of this pooled PCR product was also hybridized to a microarray (three replicate arrays performed). Sub-families containing a taxon scored as present in all three array replicates were recorded. Individual cloned rRNA genes were sequenced from each terminus, assembled using Phred and Phrap (S9, S10, S11), and were required to pass quality tests of Phred 20 (base call error probability<$10^{-2.0}$) to be included in the comparison.

Sequences that appeared chimeric were removed using Bellerophon (S2) with two requirements; (1) the preference score must be less than 1.3 and (2) the divergence ratio must be less than 1.1. The divergence ratio is a new metric implemented to weight the likelihood of a sequence being chimeric according to the similarity of the parent sequences. The more distantly related the parent sequences are to each other relative to their divergence from the chimeric sequence, the greater the likelihood that the inferred chimera is real. This metric uses the average sequence identity between the two fragments of the candidate and their corresponding parent sequences as the numerator, and the sequence identity between the parent sequences as the denominator. All calculations are made using a 300 base pair window on either side of the most likely break point. A divergence ratio of 1.1 was empirically determined to be the threshold for classifying sequences as putatively chimeric.

Similarity of clones to array taxa was calculated with DNADIST (S12) using the DNAML-F84 option assuming a transition:transversion ratio of 2.0 and an A, C, G, T 16S rRNA gene base frequency of 0.2537, 0.2317, 0.3167, 0.1979, respectively. We calculated these parameters empirically from all records of the 'Greengenes' 16S rRNA multiple sequence alignment over 1,250 nucleotides in length. The Lane mask (S13) was used to restrict similarity observations to 1,287 conserved columns (lanes) of aligned characters. Cloned sequences from this study were rejected from further analysis when <1,000 characters could be compared to a lane-masked reference sequence. Sequences were assigned to a taxonomic node using a sliding scale of similarity threshold (S14). Phylum, class, order, family, sub-family, or taxon placement was accepted when a clone surpassed similarity thresholds of 80%, 85%, 90%, 92%, 94%, or 97%, respectively. When similarity to nearest database sequence was <94%, the clone was considered to represent a novel sub-family. A full comparison between clone and array analysis is presented in Table S2.

Primers targeting sequences within particular taxa/sub-families were generated by ARB's probe design feature (S15). Melting temperatures were constrained from 45° C. to 65° C. with G+C content between 40 and 70%. The probes were chosen to contain 3' bases non-complementary to sequences outside of the taxon/sub-family. Primers were matched using Primer3 (S16) to create primer pairs (Table S3). Sequences were generated using the Takara enzyme system as described above with the necessary adjustments in annealing temperatures. Amplicons were purified (PureLink PCR Purification Kit, Invitrogen) and sequenced directly or, if there were multiple unresolved sequences, cloned using a TOPO pCR2.1 cloning kit (Invitrogen, CA) according to the manufacturer's instructions. The M13 primer pair was used for clones to generate insert amplicons for sequencing at UC Berkeley's sequencing facility.

To determine whether changes in 16S rRNA gene concentration could be detected using the array, various quantities of distinct rRNA gene types were hybridized to the array in rotating combinations. We chose environmental organisms, organisms involved in bioremediation, and a pathogen of biodefense relevance. 16S rRNA genes were amplified from each of the organisms in Table S4. Then each of these nine distinct 16S rRNA gene standards was tested once in each concentration category spanning 5 orders of magnitude (0 molecules, $6\times10^7$, $1.44\times10^8$, $3.46\times10^8$, $8.30\times10^8$, $1.99\times10^9$, $4.78\times10^9$, $2.75\times10^{10}$, $6.61\times10^{10}$, $1.59\times10^{11}$) with concentrations of individual 16S rRNA gene types rotating between arrays such that each array contained the same total of 16S rRNA gene molecules. This is similar to a Latin Square design, although with a 9×11 format matrix.

A taxon (#9389) consisting only of two sequences of *Pseudomonas oleovorans* that correlated well with environmental variables was chosen for quantitative PCR confirmation of array observed quantitative shifts. Primers for this taxon were designed using the ARB (S15) probe match function to determine unique priming sites based upon regions detected by array probes. These regions were then imputed into Primer3 (S16) in order to choose optimal oligonucleotide primers for PCR. Primer quality was further assessed using Beacon Designer v3.0 (Premier BioSoft, Calif.). Primers 9389F2 (CGACTACCTGGACTGACACT) (SEQ ID NO: 3) and 9389R2 (CACCGGCAGTCTCCTTAGAG) (SEQ ID NO: 4) were chosen to amplify a 436 bp fragment.

To test the specificity of this primer pair, we used a nested PCR approach. 16S rRNA genes were amplified using universal primers (27F, 1492R) from pooled aerosol genomic DNA extracts from both Austin and San Antonio, Tex. These products were purified and used as template in PCR reactions using primer set 9389F2-9389R2. Amplicons were then ligated to pCR2.1 and transformed into *E. coli* TOP10 cells as recommended by the manufacturer (Invitrogen, CA). Five clones were chosen at random for each of the two cities (10 clones total) and inserts were amplified using vector specific primers M13 forward and reverse. Standard Sanger sequencing was performed and sequences were tested for homology against existing database entries (NCBI GenBank, RDPII and Greengenes).

To assay *P. oleovorans* 16S rRNA gene copies in genomic DNA extracts, we performed real-time quantitative PCR (qPCR) using an iCycler iQ real-time detection system (Bio-Rad, Calif.) with the iQ Sybr® Green Supermix (BioRad, Calif.) kit. Reaction mixtures (final volume, 25 μl) contained 1×iQ Sybr® Green Supermix, 7.5 pmol of each primer, 25 ug BSA, 0.5 μl DNA extract and DNase/RNase free water. Following enzyme activation (95° C., 3 min), up to 50 cycles of 95° C., 30 s; 61° C., 30 s; 85° C., 10 s and 72° C., 45 s were performed. The specific data acquisition step (85° C. for 10 s) was set above the Tm of potential primer dimers and below the Tm of the product to minimize any non-amplicon Sybr Green fluorescence. Copy number of *P. oleovorans* 16S rRNA gene molecules was quantified by comparing cycle thresholds to a standard curve (in the range of $7.6\times10^0$ to $7.6\times10^5$ copies $\mu l^{-1}$), run in parallel, using cloned *P. oleovorans* 16S rRNA amplicons generated by PCR using primers M13 forward and reverse. Regression coefficients for the standard curves were typically greater than 0.99, and post amplification melt curve analyses displayed a single peak at 87.5° C., indicative of specific *Pseudomonas oleovorans* 16S rRNA gene amplification (data not shown).

To account for scanning intensity variation from array to array, internal standards were added to each experiment. The internal standards were a set of thirteen amplicons generated from yeast and bacterial metabolic genes and five synthetic 16S rRNA-like genes spiked into each aerosol amplicon pool prior to fragmentation. The known concentrations of the amplicons ranged from 4 pM to 605 pM in the final hybridization mix. The intensities resulting from the fifteen corresponding probe sets were natural log transformed. Adjustment factors for each array were calculated by fitting the linear model using the least-squares method. An array's adjustment factor was subtracted from each probe set's ln(intensity).

For each day of aerosol sampling, 15 factors including humidity, wind, temperature, precipitation, pressure, particulate matter, and week of year were recorded from the U.S. National Climatic Data Center (http://www.ncdc.noaa.gov) or the Texas Natural Resource Conservation Commission (http://www.tceq.state.tx.us). The weekly mean, minimum, maximum, and range of values were calculated for each factor from the collected data. The changes in ln(intensity) for each taxon considered present in the study was tested for correlation against the environmental conditions. The resulting p-values were adjusted using the step-up False Discovery Rate (FDR) controlling procedure (S18).

Multivariate regression tree analysis (S19, S20) was carried out using the package 'mvpart' within the 'R' statistical programming environment. A Bray-Curtis-based distance matrix was created using the function 'gdist'. The Brady-Curtis measure of dissimilarity is generally regarded as a good measure of ecological distance when dealing with 'species' abundance as it allows for non-linear responses to environmental gradients (S19, S21).

Prior to rarefaction analysis a distance matrix (DNAML homology) of clone sequences was created using an online tool at http://greengenes.lbl.gov/cgi-bin/nph-distance_matrix.cgi following alignment of the sequences using the NAST aligner (http://greengenes.lbl.gov/NAST) (S22). DOTUR (S23) was used to generate rarefaction curves, Chaot and ACE richness predictions and rank-abundance curves. Nearest neighbor joining was used with 1000 iterations for bootstrapping.

DNA yields in the pooled weekly filter washes ranged from 0.522 ng to 154 ng. As only an aliquot of the filter washes was extracted we extrapolate the range of DNA extractable from each daily filter to be between 150 ng and 4300 ng assuming 10% extraction efficiency. Using previous estimates of bacterial to fungal ratios in aerosols (49% bacterial, 44% fungal clones; S24) this range is equivalent to $1.2\times10^7$ to $3.5\times10^8$ bacterial cells per filter assuming a mean DNA content of a bacterial cell of 6 fg (S25).

TABLE S1

Spike in-controls of functional genes and synthetic 16S rRNA-like genes used for internal array normalization.

| | Molecules applied | Description |
|---|---|---|
| Affymetrix control spikes | | |
| AFFX-BioB-5_at | $5.83 \times 10^{10}$ | *E. coli* biotin synthetase |
| AFFX-BioB-M_at | $5.43 \times 10^{10}$ | *E. coli* biotin synthetase |
| AFFX-BioC-5_at | $2.26 \times 10^{10}$ | *E. coli* bioC protein |
| AFFX-BioC-3_at | $1.26 \times 10^{10}$ | *E. coli* bioC protein |
| AFFX-BioDn-3_at | $1.68 \times 10^{10}$ | *E. coli* dethiobiotin synthetase |
| AFFX-CreX-5_at | $2.17 \times 10^9$ | Bacteriophage P1 cre recombinase protein |
| AFFX-DapX-5_at | $9.03 \times 10^8$ | *B. subtilis* dapB, dihydrodipicolinate reductase |
| AFFX-DapX-M_at | $3.03 \times 10^{10}$ | *B. subtilis* dapB, dihydrodipicolinate reductase |

TABLE S1-continued

Spike in-controls of functional genes and synthetic 16S rRNA-like genes used for internal array normalization.

| | Molecules applied | Description |
|---|---|---|
| YFL039C | $5.02 \times 10^8$ | *Saccharomyces*, Gene for actin (Act1p) protein |
| YER022W | $1.21 \times 10^9$ | *Saccharomyces*, RNA polymerase II mediator complex subunit (SRB4p) |
| YER148W | $2.91 \times 10^9$ | *Saccharomyces*, TATA-binding protein, general transcription factor (SPT15) |
| YEL002C | $7.00 \times 10^9$ | *Saccharomyces*, Beta subunit of the oligosaccharyl transferase (OST) glycoprotein complex (WBP1) |
| YEL024W | $7.29 \times 10^{10}$ | *Saccharomyces*, Ubiquinol-cytochrome-c reductase (RIP1) |
| Synthetic 16S rRNA control spikes | | |
| SYNM.neurolyt_st | $6.74 \times 10^8$ | Synthetic derivative of *Mycoplasma neurolyticum* 16S rRNA gene |
| SYNLc.oenos_st | $3.90 \times 10^9$ | Synthetic derivative of *Leuconostoc oenos* 16S rRNA gene |
| SYNCau.cres8_st | $9.38 \times 10^9$ | Synthetic derivative of *Caulobacter crescentus* 16S rRNA gene |
| SYNFer.nodosm_st | $4.05 \times 10^{10}$ | Synthetic derivative of *Fervidobacterium nodosum* 16S rRNA gene |
| SYNSap.grandi_st | $1.62 \times 10^9$ | Synthetic derivative of *Saprospira grandis* 16S rRNA gene |

TABLE S2

Comparison between clone and array results.

| Sub-families | Array detection[1] 3/3 replicates pass = 1, fail = 0 | number of clones assigned to sub-family[2] | maximum similarity[3] | Chimera checking[4] maximum preference score[5] | maximum divergence ratio[6] | Array only pass = 1, fail = 0 | Array and Cloning pass = 1, fail = 0 | Cloning only pass = 1, fail = 0 |
|---|---|---|---|---|---|---|---|---|
| Bacteria; AD3; Unclassified; Unclassified; Unclassified; sf_1 | 1 | | | | | 1 | 0 | 0 |
| Bacteria; Acidobacteria; Acidobacteria-10; Unclassified; Unclassified; sf_1 | 1 | | | | | 1 | 0 | 0 |
| Bacteria; Acidobacteria; Acidobacteria-4; Ellin6075/11-25; Unclassified; sf_1 | 1 | | | | | 1 | 0 | 0 |
| Bacteria; Acidobacteria; Acidobacteria-6; Unclassified; Unclassified; sf_1 | 1 | | | | | 1 | 0 | 0 |
| Bacteria; Acidobacteria; Acidobacteria; Acidobacteriales; Acidobacteriaceae; sf_14 | 1 | 3 | 0.973 | 1.16 | 1.06 | 0 | 1 | 0 |
| Bacteria; Acidobacteria; Acidobacteria; Acidobacteriales; Acidobacteriaceae; sf_16 | 1 | | | | | 1 | 0 | 0 |
| Bacteria; Acidobacteria; Solibacteres; Unclassified; Unclassified; sf_1 | 1 | 2 | 0.960 | 0.00 | 0.00 | 0 | 1 | 0 |
| Bacteria; Actinobacteria; Actinobacteria; Acidimicrobiales; Acidimicrobiaceae; sf_1 | 1 | | | | | 1 | 0 | 0 |
| Bacteria; Actinobacteria; Actinobacteria; Acidimicrobiales; Microthrixineae; sf_1 | 1 | | | | | 1 | 0 | 0 |
| Bacteria; Actinobacteria; Actinobacteria; Acidimicrobiales; Microthrixineae; sf_12 | 0 | 1 | 0.947 | 0.00 | 0.00 | 0 | 0 | 1 |
| Bacteria; Actinobacteria; Actinobacteria; Acidimicrobiales; Unclassified; sf_1 | 1 | 1 | 0.961 | 1.28 | 1.06 | 0 | 1 | 0 |
| Bacteria; Actinobacteria; Actinobacteria; Actinomycetales; Acidothermaceae; sf_1 | 1 | 1 | 0.947 | 0.00 | 0.00 | 0 | 1 | 0 |
| Bacteria; Actinobacteria; Actinobacteria; Actinomycetales; Actinomycetaceae; sf_1 | 1 | | | | | 1 | 0 | 0 |
| Bacteria; Actinobacteria; Actinobacteria; Actinomycetales; Actinosynnemataceae; sf_1 | 1 | | | | | 1 | 0 | 0 |
| Bacteria; Actinobacteria; Actinobacteria; Actinomycetales; Brevibacteriaceae; sf_1 | 1 | 4 | 0.998 | 0.00 | 0.00 | 0 | 1 | 0 |
| Bacteria; Actinobacteria; Actinobacteria; Actinomycetales; Cellulomonadaceae; sf_1 | 1 | 2 | 0.981 | 1.20 | 1.08 | 0 | 1 | 0 |
| Bacteria; Actinobacteria; Actinobacteria; Actinomycetales; Corynebacteriaceae; sf_1 | 1 | | | | | 1 | 0 | 0 |
| Bacteria; Actinobacteria; Actinobacteria; Actinomycetales; Dermabacteraceae; sf_1 | 1 | 2 | 0.999 | 1.21 | 1.03 | 0 | 1 | 0 |
| Bacteria; Actinobacteria; Actinobacteria; Actinomycetales; Dermatophilaceae; sf_1 | 1 | | | | | 1 | 0 | 0 |

TABLE S2-continued

Comparison between clone and array results.

| | | Clone detection DNAML similarity | | | | Comparison | | |
| | Array detection[1] 3/3 replicates pass = 1, fail = 0 | number of clones assigned to sub-family[2] | maximum similarity[3] | Chimera checking[4] | | Array | Array and | Cloning |
| Sub-families | | | | maximum preference score[5] | maximum divergence ratio[6] | only pass = 1, fail = 0 | Cloning pass = 1, fail = 0 | only pass = 1, fail = 0 |
|---|---|---|---|---|---|---|---|---|
| Bacteria; Actinobacteria; Actinobacteria; Actinomycetales; Dietziaceae; sf_1 | 1 | | | | | 1 | 0 | 0 |
| Bacteria; Actinobacteria; Actinobacteria; Actinomycetales; Frankiaceae; sf_1 | 1 | | | | | 1 | 0 | 0 |
| Bacteria; Actinobacteria; Actinobacteria; Actinomycetales; Geodermatophilaceae; sf_1 | 1 | 2 | 1.000 | 0.00 | 0.00 | 0 | 1 | 0 |
| Bacteria; Actinobacteria; Actinobacteria; Actinomycetales; Gordoniaceae; sf_1 | 1 | | | | | 1 | 0 | 0 |
| Bacteria; Actinobacteria; Actinobacteria; Actinomycetales; Intrasporangiaceae; sf_1 | 1 | 10 | 0.999 | 1.20 | 1.18 | 0 | 1 | 0 |
| Bacteria; Actinobacteria; Actinobacteria; Actinomycetales; Kineosporiaceae; sf_1 | 1 | | | | | 1 | 0 | 0 |
| Bacteria; Actinobacteria; Actinobacteria; Actinomycetales; Microbacteriaceae; sf_1 | 1 | 4 | 0.999 | 0.00 | 0.00 | 0 | 1 | 0 |
| Bacteria; Actinobacteria; Actinobacteria; Actinomycetales; Micrococcaceae; sf_1 | 1 | 2 | 0.985 | 1.26 | 1.15 | 0 | 1 | 0 |
| Bacteria; Actinobacteria; Actinobacteria; Actinomycetales; Micromonosporaceae; sf_1 | 1 | 3 | 1.000 | 1.27 | 1.20 | 0 | 1 | 0 |
| Bacteria; Actinobacteria; Actinobacteria; Actinomycetales; Mycobacteriaceae; sf_1 | 1 | | | | | 1 | 0 | 0 |
| Bacteria; Actinobacteria; Actinobacteria; Actinomycetales; Nocardiaceae; sf_1 | 1 | 1 | 0.999 | 0.00 | 0.00 | 0 | 1 | 0 |
| Bacteria; Actinobacteria; Actinobacteria; Actinomycetales; Nocardioidaceae; sf_1 | 1 | 4 | 0.994 | 1.16 | 1.07 | 0 | 1 | 0 |
| Bacteria; Actinobacteria; Actinobacteria; Actinomycetales; Nocardiopsaceae; sf_1 | 1 | 1 | 1.000 | 0.00 | 0.00 | 0 | 1 | 0 |
| Bacteria; Actinobacteria; Actinobacteria; Actinomycetales; Promicromonosporaceae; sf_1 | 1 | | | | | 1 | 0 | 0 |
| Bacteria; Actinobacteria; Actinobacteria; Actinomycetales; Propionibacteriaceae; sf_1 | 1 | 3 | 0.982 | 1.20 | 1.05 | 0 | 1 | 0 |
| Bacteria; Actinobacteria; Actinobacteria; Actinomycetales; Pseudonocardiaceae; sf_1 | 1 | 3 | 0.999 | 1.14 | 1.11 | 0 | 1 | 0 |
| Bacteria; Actinobacteria; Actinobacteria; Actinomycetales; Sporichthyaceae; sf_1 | 1 | | | | | 1 | 0 | 0 |
| Bacteria; Actinobacteria; Actinobacteria; Actinomycetales; Streptomycetaceae; sf_1 | 1 | 3 | 0.998 | 1.30 | 1.14 | 0 | 1 | 0 |
| Bacteria; Actinobacteria; Actinobacteria; Actinomycetales; Streptomycetaceae; sf_3 | 1 | 2 | 0.996 | 0.00 | 0.00 | 0 | 1 | 0 |
| Bacteria; Actinobacteria; Actinobacteria; Actinomycetales; Streptosporangiaceae; sf_1 | 1 | | | | | 1 | 0 | 0 |
| Bacteria; Actinobacteria; Actinobacteria; Actinomycetales; Thermomonosporaceae; sf_1 | 1 | | | | | 1 | 0 | 0 |
| Bacteria; Actinobacteria; Actinobacteria; Actinomycetales; Unclassified; sf_3 | 1 | | | | | 1 | 0 | 0 |
| Bacteria; Actinobacteria; Actinobacteria; Actinomycetales; Williamsiaceae; sf_1 | 0 | 1 | 0.987 | 1.18 | 1.12 | 0 | 0 | 1 |
| Bacteria; Actinobacteria; Actinobacteria; Bifidobacteriales; Bifidobacteriaceae; sf_1 | 1 | | | | | 1 | 0 | 0 |
| Bacteria; Actinobacteria; Actinobacteria; Rubrobacterales; Rubrobacteraceae; sf_1 | 1 | 13 | 0.990 | 1.56 | 1.05 | 0 | 1 | 0 |
| Bacteria; Actinobacteria; Actinobacteria; Unclassified; Unclassified; sf_1 | 1 | | | | | 1 | 0 | 0 |
| Bacteria; Aquificae; Aquificae; Aquificales; Hydrogenothermaceae; sf_1 | 1 | | | | | 1 | 0 | 0 |
| Bacteria; BRC1; Unclassified; Unclassified; Unclassified; sf_2 | 1 | | | | | 1 | 0 | 0 |
| Bacteria; Bacteroidetes; Bacteroidetes; Bacteroidales; Porphyromonadaceae; sf_1 | 1 | | | | | 1 | 0 | 0 |
| Bacteria; Bacteroidetes; Bacteroidetes; Bacteroidales; Prevotellaceae; sf_1 | 1 | | | | | 1 | 0 | 0 |
| Bacteria; Bacteroidetes; Bacteroidetes; Bacteroidales; Rikenellaceae; sf_5 | 1 | | | | | 1 | 0 | 0 |
| Bacteria; Bacteroidetes; Bacteroidetes; Bacteroidales; Unclassified; sf_15 | 1 | | | | | 1 | 0 | 0 |

TABLE S2-continued

Comparison between clone and array results.

| Sub-families | Array detection[1] 3/3 replicates pass = 1, fail = 0 | Clone detection DNAML similarity number of clones assigned to sub-family[2] | maximum similarity[3] | Chimera checking[4] maximum preference score[5] | maximum divergence ratio[6] | Comparison Array only pass = 1, fail = 0 | Array and Cloning pass = 1, fail = 0 | Cloning only pass = 1, fail = 0 |
|---|---|---|---|---|---|---|---|---|
| Bacteria; Bacteroidetes; Flavobacteria; Flavobacteriales; Blattabacteriaceae; sf_1 | 1 | 1 | 0.943 | 0.00 | 0.00 | 0 | 1 | 0 |
| Bacteria; Bacteroidetes; Flavobacteria; Flavobacteriales; Flavobacteriaceae; sf_1 | 1 | | | | | 1 | 0 | 0 |
| Bacteria; Bacteroidetes; Flavobacteria; Flavobacteriales; Unclassified; sf_3 | 1 | | | | | 1 | 0 | 0 |
| Bacteria; Bacteroidetes; KSA1; Unclassified; Unclassified; sf_1 | 1 | | | | | 1 | 0 | 0 |
| Bacteria; Bacteroidetes; Sphingobacteria; Sphingobacteriales; Crenotrichaceae; sf_11 | 1 | 6 | 0.973 | 1.22 | 1.07 | 0 | 1 | 0 |
| Bacteria; Bacteroidetes; Sphingobacteria; Sphingobacteriales; Flammeovirgaceae; sf_5 | 1 | | | | | 1 | 0 | 0 |
| Bacteria; Bacteroidetes; Sphingobacteria; Sphingobacteriales; Flexibacteraceae; sf_19 | 1 | | | | | 1 | 0 | 0 |
| Bacteria; Bacteroidetes; Sphingobacteria; Sphingobacteriales; Sphingobacteriaceae; sf_1 | 1 | | | | | 1 | 0 | 0 |
| Bacteria; Bacteroidetes; Sphingobacteria; Sphingobacteriales; Unclassified; sf_3 | 1 | | | | | 1 | 0 | 0 |
| Bacteria; Bacteroidetes; Sphingobacteria; Sphingobacteriales; Unclassified; sf_6 | 1 | | | | | 1 | 0 | 0 |
| Bacteria; Bacteroidetes; Unclassified; Unclassified; Unclassified; sf_4 | 1 | | | | | 1 | 0 | 0 |
| Bacteria; Caldithrix; Unclassified; Caldithrales; Caldithraceae; sf_1 | 1 | | | | | 1 | 0 | 0 |
| Bacteria; Caldithrix; Unclassified; Caldithrales; Caldithraceae; sf_2 | 1 | | | | | 1 | 0 | 0 |
| Bacteria; Chlamydiae; Chlamydiae; Chlamydiales; Chlamydiaceae; sf_1 | 1 | | | | | 1 | 0 | 0 |
| Bacteria; Chlorobi; Chlorobia; Chlorobiales; Chlorobiaceae; sf_1 | 1 | | | | | 1 | 0 | 0 |
| Bacteria; Chlorobi; Unclassified; Unclassified; Unclassified; sf_1 | 1 | | | | | 1 | 0 | 0 |
| Bacteria; Chlorobi; Unclassified; Unclassified; Unclassified; sf_6 | 1 | | | | | 1 | 0 | 0 |
| Bacteria; Chlorobi; Unclassified; Unclassified; Unclassified; sf_9 | 1 | | | | | 1 | 0 | 0 |
| Bacteria; Chloroflexi; Anaerolineae; Chloroflexi-1a; Unclassified; sf_1 | 1 | 1 | 0.992 | 0.00 | 0.00 | 0 | 1 | 0 |
| Bacteria; Chloroflexi; Anaerolineae; Chloroflexi-1b; Unclassified; sf_2 | 1 | | | | | 1 | 0 | 0 |
| Bacteria; Chloroflexi; Anaerolineae; Unclassified; Unclassified; sf_9 | 1 | | | | | 1 | 0 | 0 |
| Bacteria; Chloroflexi; Chloroflexi-3; Roseiflexales; Unclassified; sf_5 | 1 | | | | | 1 | 0 | 0 |
| Bacteria; Chloroflexi; Dehalococcoidetes; Unclassified; Unclassified; sf_1 | 1 | | | | | 1 | 0 | 0 |
| Bacteria; Chloroflexi; Unclassified; Unclassified; Unclassified; sf_12 | 1 | | | | | 1 | 0 | 0 |
| Bacteria; Coprothermobacteria; Unclassified; Unclassified; Unclassified; sf_1 | 1 | | | | | 1 | 0 | 0 |
| Bacteria; Cyanobacteria; Cyanobacteria; Chloroplasts; Chloroplasts; sf_11 | 1 | | | | | 1 | 0 | 0 |
| Bacteria; Cyanobacteria; Cyanobacteria; Chloroplasts; Chloroplasts; sf_5 | 1 | 3 | 0.995 | 0.00 | 0.00 | 0 | 1 | 0 |
| Bacteria; Cyanobacteria; Cyanobacteria; Chroococcales; Unclassified; sf_1 | 1 | | | | | 1 | 0 | 0 |
| Bacteria; Cyanobacteria; Cyanobacteria; Chroococcidiopsis; Unclassified; sf_1 | 0 | 1 | 0.954 | 1.09 | 1.12 | 0 | 0 | 1 |
| Bacteria; Cyanobacteria; Cyanobacteria; Leptolyngbya; Unclassified; sf_1 | 1 | | | | | 1 | 0 | 0 |
| Bacteria; Cyanobacteria; Cyanobacteria; Nostocales; Unclassified; sf_1 | 1 | | | | | 1 | 0 | 0 |
| Bacteria; Cyanobacteria; Cyanobacteria; Oscillatoriales; Unclassified; sf_1 | 1 | | | | | 1 | 0 | 0 |

TABLE S2-continued

Comparison between clone and array results.

| | | Clone detection DNAML similarity | | | | Comparison | | |
|---|---|---|---|---|---|---|---|---|
| | Array detection[1] 3/3 replicates pass = 1, fail = 0 | number of clones assigned to sub-family[2] | maximum similarity[3] | Chimera checking[4] | | Array only pass = 1, fail = 0 | Array and Cloning pass = 1, fail = 0 | Cloning only pass = 1, fail = 0 |
| Sub-families | | | | maximum preference score[5] | maximum divergence ratio[6] | | | |
| Bacteria; Cyanobacteria; Cyanobacteria; Phormidium; Unclassified; sf_1 | 1 | | | | | 1 | 0 | 0 |
| Bacteria; Cyanobacteria; Cyanobacteria; Plectonema; Unclassified; sf_1 | 1 | | | | | 1 | 0 | 0 |
| Bacteria; Cyanobacteria; Cyanobacteria; Prochlorales; Unclassified; sf_1 | 1 | | | | | 1 | 0 | 0 |
| Bacteria; Cyanobacteria; Cyanobacteria; Pseudanabaena; Unclassified; sf_1 | 1 | | | | | 1 | 0 | 0 |
| Bacteria; Cyanobacteria; Cyanobacteria; Spirulina; Unclassified; sf_1 | 1 | | | | | 1 | 0 | 0 |
| Bacteria; Cyanobacteria; Unclassified; Unclassified; Unclassified; sf_5 | 1 | | | | | 1 | 0 | 0 |
| Bacteria; Cyanobacteria; Unclassified; Unclassified; Unclassified; sf_8 | 1 | | | | | 1 | 0 | 0 |
| Bacteria; Cyanobacteria; Unclassified; Unclassified; Unclassified; sf_9 | 1 | | | | | 1 | 0 | 0 |
| Bacteria; DSS1; Unclassified; Unclassified; Unclassified; sf_2 | 1 | | | | | 1 | 0 | 0 |
| Bacteria; Deinococcus-Thermus; Unclassified; Unclassified; Unclassified; sf_1 | 1 | | | | | 1 | 0 | 0 |
| Bacteria; Deinococcus-Thermus; Unclassified; Unclassified; Unclassified; sf_3 | 0 | 1 | 0.993 | 1.19 | 1.05 | 0 | 0 | 1 |
| Bacteria; Firmicutes; Bacilli; Bacillales; Alicyclobacillaceae; sf_1 | 1 | 2 | 0.963 | 1.14 | 1.15 | 0 | 1 | 0 |
| Bacteria; Firmicutes; Bacilli; Bacillales; Bacillaceae; sf_1 | 1 | 151 | 1.000 | 1.37 | 1.23 | 0 | 1 | 0 |
| Bacteria; Firmicutes; Bacilli; Bacillales; Halobacillaceae; sf_1 | 1 | 6 | 0.997 | 1.15 | 1.07 | 0 | 1 | 0 |
| Bacteria; Firmicutes; Bacilli; Bacillales; Paenibacillaceae; sf_1 | 1 | 14 | 0.999 | 1.19 | 1.07 | 0 | 1 | 0 |
| Bacteria; Firmicutes; Bacilli; Bacillales; Sporolactobacillaceae; sf_1 | 1 | 2 | 0.999 | 1.12 | 1.04 | 0 | 1 | 0 |
| Bacteria; Firmicutes; Bacilli; Bacillales; Staphylococcaceae; sf_1 | 1 | 6 | 0.999 | 1.30 | 1.06 | 0 | 1 | 0 |
| Bacteria; Firmicutes; Bacilli; Bacillales; Thermoactinomycetaceae; sf_1 | 1 | 6 | 0.999 | 1.15 | 1.09 | 0 | 1 | 0 |
| Bacteria; Firmicutes; Bacilli; Exiguobacterium; Unclassified; sf_1 | 0 | 1 | 0.998 | 0.00 | 0.00 | 0 | 0 | 1 |
| Bacteria; Firmicutes; Bacilli; Lactobacillales; Aerococcaceae; sf_1 | 1 | 6 | 0.998 | 1.23 | 1.26 | 0 | 1 | 0 |
| Bacteria; Firmicutes; Bacilli; Lactobacillales; Carnobacteriaceae; sf_1 | 1 | | | | | 1 | 0 | 0 |
| Bacteria; Firmicutes; Bacilli; Lactobacillales; Enterococcaceae; sf_1 | 1 | 3 | 0.999 | 1.32 | 1.08 | 0 | 1 | 0 |
| Bacteria; Firmicutes; Bacilli; Lactobacillales; Lactobacillaceae; sf_1 | 1 | | | | | 1 | 0 | 0 |
| Bacteria; Firmicutes; Bacilli; Lactobacillales; Leuconostocaceae; sf_1 | 1 | | | | | 1 | 0 | 0 |
| Bacteria; Firmicutes; Bacilli; Lactobacillales; Streptococcaceae; sf_1 | 1 | | | | | 1 | 0 | 0 |
| Bacteria; Firmicutes; Bacilli; Lactobacillales; Unclassified; sf_1 | 1 | | | | | 1 | 0 | 0 |
| Bacteria; Firmicutes; Catabacter; Unclassified; Unclassified; sf_1 | 1 | | | | | 1 | 0 | 0 |
| Bacteria; Firmicutes; Catabacter; Unclassified; Unclassified; sf_4 | 1 | 1 | 0.954 | 0.00 | 0.00 | 0 | 1 | 0 |
| Bacteria; Firmicutes; Clostridia; Clostridiales; Clostridiaceae; sf_12 | 1 | 14 | 0.998 | 1.45 | 1.15 | 0 | 1 | 0 |
| Bacteria; Firmicutes; Clostridia; Clostridiales; Eubacteriaceae; sf_1 | 1 | | | | | 1 | 0 | 0 |
| Bacteria; Firmicutes; Clostridia; Clostridiales;. Lachnospiraceae; sf_5 | 1 | 2 | 0.990 | 1.12 | 1.12 | 0 | 1 | 0 |
| Bacteria; Firmicutes; Clostridia; Clostridiales; Peptococc/Acidaminococc; sf_11 | 1 | 4 | 0.980 | 1.12 | 1.16 | 0 | 1 | 0 |

TABLE S2-continued

Comparison between clone and array results.

| Sub-families | Array detection[1] 3/3 replicates pass = 1, fail = 0 | Clone detection DNAML similarity number of clones assigned to sub-family[2] | maximum similarity[3] | Chimera checking[4] maximum preference score[5] | maximum divergence ratio[6] | Comparison Array only pass = 1, fail = 0 | Array and Cloning pass = 1, fail = 0 | Cloning only pass = 1, fail = 0 |
|---|---|---|---|---|---|---|---|---|
| Bacteria; Firmicutes; Clostridia; Clostridiales; Peptostreptococcaceae; sf_5 | 1 | 1 | 0.976 | 1.21 | 1.04 | 0 | 1 | 0 |
| Bacteria; Firmicutes; Clostridia; Clostridiales; Syntrophomonadaceae; sf_5 | 1 | | | | | 1 | 0 | 0 |
| Bacteria; Firmicutes; Clostridia; Clostridiales; Unclassified; sf_17 | 1 | | | | | 1 | 0 | 0 |
| Bacteria; Firmicutes; Clostridia; Unclassified; Unclassified; sf_3 | 1 | | | | | 1 | 0 | 0 |
| Bacteria; Firmicutes; Desulfotomaculum; Unclassified; Unclassified; sf_1 | 1 | 3 | 0.984 | 1.14 | 1.04 | 0 | 1 | 0 |
| Bacteria; Firmicutes; Mollicutes; Acholeplasmatales; Acholeplasmataceae; sf_1 | 1 | | | | | 1 | 0 | 0 |
| Bacteria; Firmicutes; Symbiobacteria; Symbiobacterales; Unclassified; sf_1 | 1 | | | | | 1 | 0 | 0 |
| Bacteria; Firmicutes; Unclassified; Unclassified; Unclassified; sf_8 | 1 | | | | | 1 | 0 | 0 |
| Bacteria; Firmicutes; gut clone group; Unclassified; Unclassified; sf_1 | 1 | | | | | 1 | 0 | 0 |
| Bacteria; Gemmatimonadetes; Unclassified; Unclassified; Unclassified; sf_5 | 1 | | | | | 1 | 0 | 0 |
| Bacteria; Natronoanaerobium; Unclassified; Unclassified; Unclassified; sf_1 | 1 | | | | | 1 | 0 | 0 |
| Bacteria; Nitrospira; Nitrospira; Nitrospirales; Nitrospiraceae; sf_1 | 1 | | | | | 1 | 0 | 0 |
| Bacteria; OD1; OP11-5; Unclassified; Unclassified; sf_1 | 1 | | | | | 1 | 0 | 0 |
| Bacteria; OP8; Unclassified; Unclassified; Unclassified; sf_3 | 1 | | | | | 1 | 0 | 0 |
| Bacteria; Planctomycetes; Planctomycetacia; Planctomycetales; Anammoxales; sf_2 | 1 | | | | | 1 | 0 | 0 |
| Bacteria; Planctomycetes; Planctomycetacia; Planctomycetales; Anammoxales; sf_4 | 1 | | | | | 1 | 0 | 0 |
| Bacteria; Planctomycetes; Planctomycetacia; Planctomycetales; Pirellulae; sf_3 | 1 | | | | | 1 | 0 | 0 |
| Bacteria; Planctomycetes; Planctomycetacia; Planctomycetales; Planctomycetaceae; sf_3 | 1 | | | | | 1 | 0 | 0 |
| Bacteria; Proteobacteria; Alphaproteobacteria; Acetobacterales; Acetobacteraceae; sf_1 | 1 | 1 | 0.943 | 0.00 | 0.00 | 0 | 1 | 0 |
| Bacteria; Proteobacteria; Alphaproteobacteria; Acetobacterales; Roseococcaceae; sf_1 | 1 | 6 | 0.980 | 1.24 | 1.17 | 0 | 1 | 0 |
| Bacteria; Proteobacteria; Alphaproteobacteria; Azospirillales; Azospirillaceae; sf_1 | 1 | 1 | 0.947 | 1.12 | 1.10 | 0 | 1 | 0 |
| Bacteria; Proteobacteria; Alphaproteobacteria; Azospirillales; Magnetospirillaceae; sf_1 | 1 | | | | | 1 | 0 | 0 |
| Bacteria; Proteobacteria; Alphaproteobacteria; Azospirillales; Unclassified; sf_1 | 1 | | | | | 1 | 0 | 0 |
| Bacteria; Proteobacteria; Alphaproteobacteria; Bradyrhizobiales; Beijerinck/Rhodoplan/Methylocyst; sf_3 | 1 | 2 | 0.951 | 1.13 | 1.08 | 0 | 1 | 0 |
| Bacteria; Proteobacteria; Alphaproteobacteria; Bradyrhizobiales; Bradyrhizobiaceae; sf_1 | 1 | | | | | 1 | 0 | 0 |
| Bacteria; Proteobacteria; Alphaproteobacteria; Bradyrhizobiales; Hyphomicrobiaceae; sf_1 | 1 | | | | | 1 | 0 | 0 |
| Bacteria; Proteobacteria; Alphaproteobacteria; Bradyrhizobiales; Methylobacteriaceae; sf_1 | 1 | 2 | 0.999 | 0.00 | 0.00 | 0 | 1 | 0 |
| Bacteria; Proteobacteria; Alphaproteobacteria; Bradyrhizobiales; Unclassified; sf_1 | 1 | 4 | 0.982 | 1.15 | 1.11 | 0 | 1 | 0 |
| Bacteria; Proteobacteria; Alphaproteobacteria; Bradyrhizobiales; Xanthobacteraceae; sf_1 | 1 | | | | | 1 | 0 | 0 |
| Bacteria; Proteobacteria; Alphaproteobacteria; Caulobacterales; Caulobacteraceae; sf_1 | 1 | 1 | 0.968 | 0.00 | 0.00 | 0 | 1 | 0 |
| Bacteria; Proteobacteria; Alphaproteobacteria; Consistiales; Caedibacteraceae; sf_3 | 1 | 1 | 0.951 | 0.00 | 0.00 | 0 | 1 | 0 |
| Bacteria; Proteobacteria; Alphaproteobacteria; Consistiales; Caedibacteraceae; sf_4 | 1 | | | | | 1 | 0 | 0 |

TABLE S2-continued

Comparison between clone and array results.

| Sub-families | Array detection[1] 3/3 replicates pass = 1, fail = 0 | Clone detection DNAML similarity number of clones assigned to sub-family[2] | maximum similarity[3] | Chimera checking[4] maximum preference score[5] | maximum divergence ratio[6] | Comparison Array only pass = 1, fail = 0 | Array and Cloning pass = 1, fail = 0 | Cloning only pass = 1, fail = 0 |
|---|---|---|---|---|---|---|---|---|
| Bacteria; Proteobacteria; Alphaproteobacteria; Consistiales; Caedibacteraceae; sf_5 | 1 | | | | | 1 | 0 | 0 |
| Bacteria; Proteobacteria; Alphaproteobacteria; Consistiales; Unclassified; sf_4 | 1 | | | | | 1 | 0 | 0 |
| Bacteria; Proteobacteria; Alphaproteobacteria; Devosia; Unclassified; sf_1 | 1 | 1 | 0.976 | 1.18 | 1.05 | 0 | 1 | 0 |
| Bacteria; Proteobacteria; Alphaproteobacteria; Ellin314/wr0007; Unclassified; sf_1 | 1 | | | | | 1 | 0 | 0 |
| Bacteria; Proteobacteria; Alphaproteobacteria; Ellin329/Riz1046; Unclassified; sf_1 | 1 | | | | | 1 | 0 | 0 |
| Bacteria; Proteobacteria; Alphaproteobacteria; Fulvimarina; Unclassified; sf_1 | 1 | | | | | 1 | 0 | 0 |
| Bacteria; Proteobacteria; Alphaproteobacteria; Rhizobiales; Bartonellaceae; sf_1 | 1 | | | | | 1 | 0 | 0 |
| Bacteria; Proteobacteria; Alphaproteobacteria; Rhizobiales; Beijerinck/Rhodoplan/Methylocyst; sf_1 | 1 | | | | | 1 | 0 | 0 |
| Bacteria; Proteobacteria; Alphaproteobacteria; Rhizobiales; Bradyrhizobiaceae; sf_1 | 1 | | | | | 1 | 0 | 0 |
| Bacteria; Proteobacteria; Alphaproteobacteria; Rhizobiales; Brucellaceae; sf_1 | 1 | | | | | 1 | 0 | 0 |
| Bacteria; Proteobacteria; Alphaproteobacteria; Rhizobiales; Hyphomicrobiaceae; sf_1 | 1 | | | | | 1 | 0 | 0 |
| Bacteria; Proteobacteria; Alphaproteobacteria; Rhizobiales; Phyllobacteriaceae; sf_1 | 1 | | | | | 1 | 0 | 0 |
| Bacteria; Proteobacteria; Alphaproteobacteria; Rhizobiales; Rhizobiaceae; sf_1 | 1 | 2 | 0.981 | 1.27 | 1.26 | 0 | 1 | 0 |
| Bacteria; Proteobacteria; Alphaproteobacteria; Rhizobiales; Unclassified; sf_1 | 1 | | | | | 1 | 0 | 0 |
| Bacteria; Proteobacteria; Alphaproteobacteria; Rhodobacterales; Hyphomonadaceae; sf_1 | 1 | | | | | 1 | 0 | 0 |
| Bacteria; Proteobacteria; Alphaproteobacteria; Rhodobacterales; Rhodobacteraceae; sf_1 | 1 | 6 | 0.985 | 1.13 | 1.11 | 0 | 1 | 0 |
| Bacteria; Proteobacteria; Alphaproteobacteria; Rickettsiales; Anaplasmataceae; sf_3 | 1 | | | | | 1 | 0 | 0 |
| Bacteria; Proteobacteria; Alphaproteobacteria; Rickettsiales; Rickettsiaceae; sf_1 | 1 | | | | | 1 | 0 | 0 |
| Bacteria; Proteobacteria; Alphaproteobacteria; Rickettsiales; Unclassified; sf_2 | 1 | | | | | 1 | 0 | 0 |
| Bacteria; Proteobacteria; Alphaproteobacteria; Sphingomonadales; Sphingomonadaceae; sf_1 | 1 | 9 | 0.994 | 1.23 | 1.10 | 0 | 1 | 0 |
| Bacteria; Proteobacteria; Alphaproteobacteria; Sphingomonadales; Sphingomonadaceae; sf_15 | 1 | 6 | 0.990 | 1.13 | 1.06 | 0 | 1 | 0 |
| Bacteria; Proteobacteria; Alphaproteobacteria; Sphingomonadales; Unclassified; sf_1 | 0 | 3 | 0.997 | 1.20 | 1.08 | 0 | 0 | 1 |
| Bacteria; Proteobacteria; Alphaproteobacteria; Unclassified; Unclassified; sf_6 | 1 | 1 | 0.954 | 0.00 | 0.00 | 0 | 1 | 0 |
| Bacteria; Proteobacteria; Betaproteobacteria; Burkholderiales; Alcaligenaceae; sf_1 | 1 | 3 | 1.000 | 1.35 | 1.07 | 0 | 1 | 0 |
| Bacteria; Proteobacteria; Betaproteobacteria; Burkholderiales; Burkholderiaceae; sf_1 | 1 | 12 | 1.000 | 0.00 | 0.00 | 0 | 1 | 0 |
| Bacteria; Proteobacteria; Betaproteobacteria; Burkholderiales; Comamonadaceae; sf_1 | 1 | | | | | 1 | 0 | 0 |
| Bacteria; Proteobacteria; Betaproteobacteria; Burkholderiales; Oxalobacteraceae; sf_1 | 1 | 2 | 0.996 | 0.00 | 0.00 | 0 | 1 | 0 |
| Bacteria; Proteobacteria; Betaproteobacteria; Burkholderiales; Ralstoniaceae; sf_1 | 1 | | | | | 1 | 0 | 0 |
| Bacteria; Proteobacteria; Betaproteobacteria; MND1 clone group; Unclassified; sf_1 | 1 | | | | | 1 | 0 | 0 |
| Bacteria; Proteobacteria; Betaproteobacteria; Methylophilales; Methylophilaceae; sf_1 | 1 | | | | | 1 | 0 | 0 |
| Bacteria; Proteobacteria; Betaproteobacteria; Neisseriales; Unclassified; sf_1 | 1 | | | | | 1 | 0 | 0 |
| Bacteria; Proteobacteria; Betaproteobacteria; Nitrosomonadales; Nitrosomonadaceae; sf_1 | 1 | | | | | 1 | 0 | 0 |

TABLE S2-continued

Comparison between clone and array results.

| Sub-families | Array detection[1] 3/3 replicates pass = 1, fail = 0 | Clone detection DNAML similarity number of clones assigned to sub-family[2] | maximum similarity[3] | Chimera checking[4] maximum preference score[5] | maximum divergence ratio[6] | Comparison Array only pass = 1, fail = 0 | Array and Cloning pass = 1, fail = 0 | Cloning only pass = 1, fail = 0 |
|---|---|---|---|---|---|---|---|---|
| Bacteria; Proteobacteria; Betaproteobacteria; Rhodocyclales; Rhodocyclaceae; sf_1 | 1 | | | | | 1 | 0 | 0 |
| Bacteria; Proteobacteria; Betaproteobacteria; Unclassified; Unclassified; sf_3 | 1 | | | | | 1 | 0 | 0 |
| Bacteria; Proteobacteria; Deltaproteobacteria; AMD clone group; Unclassified; sf_1 | 1 | | | | | 1 | 0 | 0 |
| Bacteria; Proteobacteria; Deltaproteobacteria; Bdellovibrionales; Unclassified; sf_1 | 1 | | | | | 1 | 0 | 0 |
| Bacteria; Proteobacteria; Deltaproteobacteria; Desulfobacterales; Desulfobulbaceae; sf_1 | 1 | | | | | 1 | 0 | 0 |
| Bacteria; Proteobacteria; Deltaproteobacteria; Desulfobacterales; Nitrospinaceae; sf_2 | 1 | | | | | 1 | 0 | 0 |
| Bacteria; Proteobacteria; Deltaproteobacteria; Desulfobacterales; Unclassified; sf_4 | 1 | | | | | 1 | 0 | 0 |
| Bacteria; Proteobacteria; Deltaproteobacteria; Desulfovibrionales; Desulfohalobiaceae; sf_1 | 1 | | | | | 1 | 0 | 0 |
| Bacteria; Proteobacteria; Deltaproteobacteria; Desulfovibrionales; Desulfovibrionaceae; sf_1 | 1 | | | | | 1 | 0 | 0 |
| Bacteria; Proteobacteria; Deltaproteobacteria; Desulfovibrionales; Unclassified; sf_1 | 1 | | | | | 1 | 0 | 0 |
| Bacteria; Proteobacteria; Deltaproteobacteria; EB1021 group; Unclassified; sf_4 | 1 | | | | | 1 | 0 | 0 |
| Bacteria; Proteobacteria; Deltaproteobacteria; Myxococcales; Myxococcaceae; sf_1 | 0 | 1 | 0.974 | 0.00 | 0.00 | 0 | 0 | 1 |
| Bacteria; Proteobacteria; Deltaproteobacteria; Myxococcales; Polyangiaceae; sf_3 | 1 | | | | | 1 | 0 | 0 |
| Bacteria; Proteobacteria; Deltaproteobacteria; Myxococcales; Unclassified; sf_1 | 1 | | | | | 1 | 0 | 0 |
| Bacteria; Proteobacteria; Deltaproteobacteria; Syntrophobacterales; Syntrophobacteraceae; sf_1 | 1 | | | | | 1 | 0 | 0 |
| Bacteria; Proteobacteria; Deltaproteobacteria; Unclassified; Unclassified; sf_9 | 1 | | | | | 1 | 0 | 0 |
| Bacteria; Proteobacteria; Deltaproteobacteria; dechlorinating clone group; Unclassified; sf_1 | 1 | | | | | 1 | 0 | 0 |
| Bacteria; Proteobacteria; Epsilonproteobacteria; Campylobacterales; Campylobacteraceae; sf_3 | 1 | | | | | 1 | 0 | 0 |
| Bacteria; Proteobacteria; Epsilonproteobacteria; Campylobacterales; Helicobacteraceae; sf_3 | 1 | | | | | 1 | 0 | 0 |
| Bacteria; Proteobacteria; Epsilonproteobacteria; Campylobacterales; Unclassified; sf_1 | 1 | | | | | 1 | 0 | 0 |
| Bacteria; Proteobacteria; Gammaproteobacteria; Aeromonadales; Aeromonadaceae; sf_1 | 1 | | | | | 1 | 0 | 0 |
| Bacteria; Proteobacteria; Gammaproteobacteria; Alteromonadales; Alteromonadaceae; sf_1 | 1 | | | | | 1 | 0 | 0 |
| Bacteria; Proteobacteria; Gammaproteobacteria; Alteromonadales; Pseudoalteromonadaceae; sf_1 | 1 | | | | | 1 | 0 | 0 |
| Bacteria; Proteobacteria; Gammaproteobacteria; Alteromonadales; Unclassified; sf_1 | 1 | | | | | 1 | 0 | 0 |
| Bacteria; Proteobacteria; Gammaproteobacteria; Chromatiales; Chromatiaceae; sf_1 | 1 | | | | | 1 | 0 | 0 |
| Bacteria; Proteobacteria; Gammaproteobacteria; Chromatiales; Ectothiorhodospiraceae; sf_1 | 1 | | | | | 1 | 0 | 0 |
| Bacteria; Proteobacteria; Gammaproteobacteria; Chromatiales; Unclassified; sf_1 | 1 | | | | | 1 | 0 | 0 |
| Bacteria; Proteobacteria; Gammaproteobacteria; Ellin307/WD2124; Unclassified; sf_1 | 1 | | | | | 1 | 0 | 0 |
| Bacteria; Proteobacteria; Gammaproteobacteria; Enterobacteriales; Enterobacteriaceae; sf_1 | 1 | 3 | 0.995 | 1.12 | 1.04 | 0 | 1 | 0 |
| Bacteria; Proteobacteria; Gammaproteobacteria; Enterobacteriales; Enterobacteriaceae; sf_6 | 1 | | | | | 1 | 0 | 0 |
| Bacteria; Proteobacteria; Gammaproteobacteria; GAO cluster; Unclassified; sf_1 | 1 | | | | | 1 | 0 | 0 |

TABLE S2-continued

Comparison between clone and array results.

| | Array detection[1] 3/3 replicates pass = 1, fail = 0 | Clone detection DNAML similarity | | Chimera checking[4] | | Comparison | | |
|---|---|---|---|---|---|---|---|---|
| | | number of clones assigned to sub-family[2] | maximum similarity[3] | maximum preference score[5] | maximum divergence ratio[6] | Array only pass = 1, fail = 0 | Array and Cloning pass = 1, fail = 0 | Cloning only pass = 1, fail = 0 |
| Sub-families | | | | | | | | |
| Bacteria; Proteobacteria; Gammaproteobacteria; Legionellales; Coxiellaceae; sf_3 | 1 | | | | | 1 | 0 | 0 |
| Bacteria; Proteobacteria; Gammaproteobacteria; Legionellales; Unclassified; sf_1 | 1 | | | | | 1 | 0 | 0 |
| Bacteria; Proteobacteria; Gammaproteobacteria; Legionellales; Unclassified; sf_3 | 1 | | | | | 1 | 0 | 0 |
| Bacteria; Proteobacteria; Gammaproteobacteria; Methylococcales; Methylococcaceae; sf_1 | 1 | | | | | 1 | 0 | 0 |
| Bacteria; Proteobacteria; Gammaproteobacteria; Oceanospirillales; Alcanivoraceae; sf_1 | 1 | | | | | 1 | 0 | 0 |
| Bacteria; Proteobacteria; Gammaproteobacteria; Oceanospirillales; Halomonadaceae; sf_1 | 1 | | | | | 1 | 0 | 0 |
| Bacteria; Proteobacteria; Gammaproteobacteria; Oceanospirillales; Unclassified; sf_3 | 1 | | | | | 1 | 0 | 0 |
| Bacteria; Proteobacteria; Gammaproteobacteria; Pasteurellales; Pasteurellaceae; sf_1 | 1 | | | | | 1 | 0 | 0 |
| Bacteria; Proteobacteria; Gammaproteobacteria; Pseudomonadales; Moraxellaceae; sf_3 | 1 | 2 | 0.996 | 1.16 | 1.10 | 0 | 1 | 0 |
| Bacteria; Proteobacteria; Gammaproteobacteria; Pseudomonadales; Pseudomonadaceae; sf_1 | 1 | 2 | 0.998 | 1.18 | 1.03 | 0 | 1 | 0 |
| Bacteria; Proteobacteria; Gammaproteobacteria; SUP05; Unclassified; sf_1 | 1 | | | | | 1 | 0 | 0 |
| Bacteria; Proteobacteria; Gammaproteobacteria; Shewanella; Unclassified; sf_1 | 1 | | | | | 1 | 0 | 0 |
| Bacteria; Proteobacteria; Gammaproteobacteria; Symbionts; Unclassified; sf_1 | 1 | | | | | 1 | 0 | 0 |
| Bacteria; Proteobacteria; Gammaproteobacteria; Thiotrichales; Francisellaceae; sf_1 | 1 | | | | | 1 | 0 | 0 |
| Bacteria; Proteobacteria; Gammaproteobacteria; Thiotrichales; Piscirickettsiaceae; sf_3 | 1 | | | | | 1 | 0 | 0 |
| Bacteria; Proteobacteria; Gammaproteobacteria; Thiotrichales; Thiotrichaceae; sf_3 | 1 | | | | | 1 | 0 | 0 |
| Bacteria; Proteobacteria; Gammaproteobacteria; Unclassified; Unclassified; sf_3 | 1 | | | | | 1 | 0 | 0 |
| Bacteria; Proteobacteria; Gammaproteobacteria; Xanthomonadales; Xanthomonadaceae; sf_3 | 1 | 2 | 0.997 | 0.00 | 0.00 | 0 | 1 | 0 |
| Bacteria; Proteobacteria; Gammaproteobacteria; aquatic clone group; Unclassified; sf_1 | 1 | | | | | 1 | 0 | 0 |
| Bacteria; Proteobacteria; Gammaproteobacteria; uranium waste clones; Unclassified; sf_1 | 1 | | | | | 1 | 0 | 0 |
| Bacteria; Proteobacteria; Unclassified; Unclassified; Unclassified; sf_20 | 1 | | | | | 1 | 0 | 0 |
| Bacteria; Spirochaetes; Spirochaetes; Spirochaetales; Leptospiraceae; sf_3 | 1 | | | | | 1 | 0 | 0 |
| Bacteria; Spirochaetes; Spirochaetes; Spirochaetales; Spirochaetaceae; sf_1 | 1 | | | | | 1 | 0 | 0 |
| Bacteria; Spirochaetes; Spirochaetes; Spirochaetales; Spirochaetaceae; sf_3 | 1 | | | | | 1 | 0 | 0 |
| Bacteria; TM7; TM7-3; Unclassified; Unclassified; sf_1 | 1 | | | | | 1 | 0 | 0 |
| Bacteria; TM7; Unclassified; Unclassified; Unclassified; sf_1 | 1 | | | | | 1 | 0 | 0 |
| Bacteria; Verrucomicrobia; Unclassified; Unclassified; Unclassified; sf_4 | 1 | | | | | 1 | 0 | 0 |
| Bacteria; Verrucomicrobia; Unclassified; Unclassified; Unclassified; sf_5 | 1 | | | | | 1 | 0 | 0 |
| Bacteria; Verrucomicrobia; Verrucomicrobiae; Verrucomicrobiales; Unclassified; sf_3 | 1 | | | | | 1 | 0 | 0 |
| Bacteria; Verrucomicrobia; Verrucomicrobiae; Verrucomicrobiales; Verrucomicrobia subdivision 5; sf_1 | 1 | | | | | 1 | 0 | 0 |
| Bacteria; Verrucomicrobia; Verrucomicrobiae; Verrucomicrobiales; Verrucomicrobiaceae; sf_6 | 1 | | | | | 1 | 0 | 0 |
| Bacteria; Verrucomicrobia; Verrucomicrobiae; Verrucomicrobiales; Verrucomicrobiaceae; sf_7 | 1 | | | | | 1 | 0 | 0 |

TABLE S2-continued

Comparison between clone and array results.

| Sub-families | Array detection[1] 3/3 replicates pass = 1, fail = 0 | Clone detection DNAML similarity — number of clones assigned to sub-family[2] | Clone detection DNAML similarity — maximum similarity[3] | Chimera checking[4] — maximum preference score[5] | Chimera checking[4] — maximum divergence ratio[6] | Comparison — Array only pass = 1, fail = 0 | Comparison — Array and Cloning pass = 1, fail = 0 | Comparison — Cloning only pass = 1, fail = 0 |
|---|---|---|---|---|---|---|---|---|
| Bacteria; WS3; Unclassified; Unclassified; Unclassified; sf_1 | 1 | | | | | 1 | 0 | 0 |
| Bacteria; marine group A; mgA-1; Unclassified; Unclassified; sf_1 | 1 | | | | | 1 | 0 | 0 |
| Bacteria; marine group A; mgA-2; Unclassified; Unclassified; sf_1 | 1 | | | | | 1 | 0 | 0 |
| Totals | 238 Array sub-families | 67 Clone sub-families | | | | 178 Array only sub-families | 60 Array and clone sub-families | 7 Clone only sub-families |

[1]A sub-family must have at least one taxon present above the positive probe threshold of 0.92 (92%) in all three replicates to be considered present.
[2]For a clone to be assigned to a sub-family its DNAML similarity must be above the 0.94 (94%) threshold defined for sub-families.
[3]This is the maximum DNAML similarity measured.
[4]Both maximum preference score and maximum divergence ratio must pass the criteria below for a clone to be considered non-chimeric.
[5]Bellerophon preference score, a ratio of 1.3 or greater has been empirically shown to demonstrate a chimeric molecule.
[6]Bellerophon divergence ratio.
This is a new metric devised to aid chimera detection, a score greater than 1.1 indicates a potential chimera.

TABLE S3

Confirmation of array sub-family detections by taxon-specific PCR and sequencing.

| Genbank accession number of retrieved sequence | Sub-family (sf) verified | Closest BLAST homolog GenBank accession number (% identity) | SEQ ID NO. | Primer Sequences (5' to 3') | Tm °C. | Ta °C. |
|---|---|---|---|---|---|---|
| DQ236248 | Actinobacteria, Actinosynnemataceae, sf_1 | Actinokineospora diospyrosa, AF114797 (94.3%) | 5 6 | For-ACCAAGGCTACGACGGGTA Rev-ACACACCGCATGTCAAACC | 60.5 60.4 | 67.0 |
| DQ515230 | Actinobacteria, Bifidobacteriaceae, sf_1 | Bifidobacterium adolescentis, AF275881 (99.6 %) | 7 8 | For-GGGTGGTAATGCCSGATG Rev-CCRCCGTTACACCGGGAA | 60.0 64.0 | 62.0 |
| DQ236245 | Actinobacteria, Kineosporiaceae, sf_1 | Actinomycetaceae SR 11, X87617 (97.7%) | 9 10 | For-CAATGGACTCAAGCCTGATG Rev-CTCTAGCCTGCCCGTTTC | 53.5 53.9 | 53.0 |
| DQ236250 | Chloroflexi, Anaerolineae, sf_9 | penguin droppings clone KD4-96, AY218649 (90%) | 11 12 | For-GAGAGGATGATCAGCCAG Rev-TACGGYTACCTTGTTACGACTT | 54.0 57.0 | 61.7 |
| DQ236247 | Cyanobacteria, Geitlerinema, sf_1 | Geitlerinema sp. PCC 7105, AB039010 (89.3%) | 13 14 | For-TCCGTAGGTGGCTGTTCAAGTCTG Rev-GCTTTCGTCCCTCAGTGTCAGTTG | 62.2 61.7 | 55.0 |
| DQ236246 | Cyanobacteria, Thermosynechococcus, sf_1 | Thermosynechococcus elongatus BP-1, BA000039 (96.0%) | 15 16 | For-TGTCGTGAGATGTTGGGTAAGTC Rev-TGAGCCGTGGTTTAAGAGATTAGC | 58.7 58.8 | 55.0 |
| DQ129654 | Gammaproteobacteria, Pseudoaltermonadaceae sf_1 | Pseudoalteromonas sp. S511-1, AB029824 (99.1%) | 17 18 | For-GCCTCACGCCATAAGATTAG Rev-GTGCTTTCTTCTGTAAGTAACG | 53.1 53.0 | 50.0 |
| DQ129656 | Nitrospira, Nitrospiraceae, sf_1 | Nitrospira moscoviensis, X82558 (98.5%) | 19 20 | For-TCGAAAAGCGTGGGG Rev-CTTCCTCCCCCGTTC | 57.6 54.4 | 47.0 |

TABLE S3-continued

Confirmation of array sub-family detections by taxon-specific PCR and sequencing.

| Genbank accession number of retrieved sequence | Sub-family (sf) verified | Closest BLAST homolog GenBank accession number (% identity) | SEQ ID NO. | Primer Sequences (5' to 3') | Tm °C. | Ta °C. |
|---|---|---|---|---|---|---|
| DQ129666 | Planctomycetes, Plantomycetaceae, sf_3 | *Planctomyces brasiltensis*, AJ231190 (94%) | 21 22 | For-GAAACTGCCCAGACAC Rev-AGTAACGTTCGCACAG | 50.0 48.0 | 60.0 |
| DQ515231 | Proteobacteria, Campylobacteraceae sf_3 | Uncultured *Arcobacter* sp. clone DS017, DQ234101 (98%) | 23 24 | For-GGATGACACTTTTCGGAG Rev-AATTCCATCTGCCTCTCC | 54.0 55.0 | 48.0 |
| DQ129662 | Spirochaetes, Leptospiracea, sf_3 | *Leptospira borgpetersenii* X17547 (90.9%) | 25 26 | For-GGCGGCGCGTTTTAAGC Rev-ACTCGGGTGGTGTGACG | 57.0 57.0 | 58.7 |
| DQ129661 | Spirochaetes, Spirochaetaceae, sf_1 | *Spirochaeta asiatica*, X93926 (90.0%) | | | | |
| DQ129660 | Spirochaetes, Spirochaetaceae, sf_3 | *Borrelia hermsii* M72398 (91.0%) | | | | |
| DQ236249 | TM7, TM7-3 sf_1 | oral clone EW096, AY349415 (88.8%) | 27 28 | For-AYTGGGCGTAAAGAGTTGC Rev-TACGGYTACCTTGTTACGACTT | 58.0 57.0 | 66.3 |

Tm = Melting temperature; Ta = Optimal annealing temperature used in PCR reaction.

TABLE S4

Bacteria and Archaea used for Latin square hybridization assays.

| Organism | Phylum/Sub-phylum | ATCC |
|---|---|---|
| *Arthrobacter oxydans* | Actinobacteria | 14359[a] |
| *Bacillus anthracis* AMES pX01- pX02- | Firmicutes | —[b] |
| *Caulobacter crescentus* CB15 | Alpha-proteobacteria | 19089 |
| *Dechloromonas agitata* CKB | Beta-proteobacteria | 700666[c] |
| *Dehalococcoides ethenogenes* 195 | Chloroflexi | —[d] |
| *Desulfovibrio vulgaris* Hildenborough | Delta-proteobacteria | 29579[e] |
| *Francisella tularensis* | Gamma-proteobacteria | 6223 |
| *Geobacter metallireducens* GS-15 | Delta-proteobacteria | 53774[e] |
| *Geothrix fermentans* H-5 | Acidobacteria | 700665[e] |
| *Sulfolobus solfataricus* | Crenarchaeota | 35092 |

[a] Stain obtained from Hoi-Ying Holman, LBNL.
[b] Strain obtained from Arthur Friedlander USAMRID.
[c] Strain obtained from John Coates, UC Berkeley.
[d] Strain obtained from Lisa Alvarez-Cohen, UC Berkeley.
[e] Strain obtained from Terry Hazen, LBNL.

TABLE S5

Correlations between environmental/temporal parameters.

| | week | mean TEMP | max MAXTEMP | min MINTEMP | range MINTEMP | mean WDSP | mean SLP | max VISIB | max PM2.5 | range PM2.5 | Sub-family-level richness |
|---|---|---|---|---|---|---|---|---|---|---|---|
| Austin | | | | | | | | | | | |
| week | 1.000 | | | | | | | | | | |
| mean TEMP | 0.703 | 1.000 | | | | | | | | | |
| max MAXTEMP | 0.471 | 0.665 | 1.000 | | | | | | | | |
| min MINTEMP | 0.685 | 0.691 | 0.073 | 1.000 | | | | | | | |
| range MINTEMP | -0.267 | -0.149 | 0.571 | -0.777 | 1.000 | | | | | | |
| mean WDSP | -0.540 | -0.053 | -0.038 | -0.195 | 0.136 | 1.000 | | | | | |
| mean SLP | 0.607 | 0.145 | 0.162 | 0.352 | -0.188 | -0.380 | 1.000 | | | | |
| max VISIB | 0.486 | 0.311 | 0.400 | 0.230 | 0.063 | -0.498 | 0.318 | 1.000 | | | |
| max PM2.5 | -0.529 | -0.219 | -0.331 | -0.162 | -0.075 | 0.617 | -0.409 | -0.817 | 1.000 | | |
| range PM2.5 | -0.507 | -0.219 | -0.366 | -0.117 | -0.134 | 0.613 | -0.407 | -0.829 | 0.989 | 1.000 | |
| Sub-family-level richness | -0.074 | -0.104 | 0.098 | -0.460 | 0.440 | 0.251 | -0.182 | -0.066 | -0.058 | -0.063 | 1.000 |
| San Antonio | | | | | | | | | | | |
| week | 1.000 | | | | | | | | | | |
| mean TEMP | 0.452 | 1.000 | | | | | | | | | |
| max | 0.189 | 0.553 | 1.000 | | | | | | | | |

TABLE S5-continued

Correlations between environmental/temporal parameters.

|  | week | mean TEMP | max MAXTEMP | min MINTEMP | range MINTEMP | mean WDSP | mean SLP | max VISIB | max PM2.5 | range PM2.5 | Sub-family-level richness |
|---|---|---|---|---|---|---|---|---|---|---|---|
| MAXTEMP min MINTEMP | 0.570 | 0.622 | 0.044 | 1.000 | | | | | | | |
| range MINTEMP | −0.318 | −0.116 | 0.630 | −0.749 | 1.000 | | | | | | |
| mean WDSP | −0.523 | −0.014 | −0.015 | −0.014 | 0.001 | 1.000 | | | | | |
| mean SLP | 0.722 | 0.029 | −0.088 | 0.300 | −0.291 | −0.495 | 1.000 | | | | |
| max VISIB | 0.420 | 0.169 | 0.298 | −0.054 | 0.240 | −0.234 | 0.501 | 1.000 | | | |
| max PM2.5 | −0.508 | −0.157 | −0.197 | −0.022 | −0.114 | 0.189 | −0.420 | −0.830 | 1.000 | | |
| range PM2.5 | −0.515 | −0.164 | −0.201 | 0.000 | −0.134 | 0.255 | −0.455 | −0.843 | 0.991 | 1.000 | |
| Sub-family-level richness | 0.125 | −0.016 | −0.050 | 0.024 | −0.051 | −0.419 | 0.175 | −0.054 | −0.064 | −0.102 | 1.000 |

Underlined font indicates a significant positive correlation, while italic font indicates a significant negative correlation at a 95% confidence interval.

TABLE S6

Sub-families detected in Austin or San Antonio correlating significantly with environmental parameters.
All of the below are in the Domain of Bacteria

| Phylum | Class | Order | Family | Sub-family | taxon and representative organism name | Environ. factor | Correl. Coeff. | p value | BH adjusted p. value[a] |
|---|---|---|---|---|---|---|---|---|---|
| Actinobacteria | Actinobacteria | Actinomycetales | Unclassified | sf_3 | 1114 clone PENDANT-38 | max TEMP | 0.64 | 4.05E−05 | 2.49E−02 |
| Actinobacteria | Actinobacteria | Actinomycetales | Unclassified | sf_3 | 1114 clone PENDANT-38 | mean TEMP | 0.66 | 2.16E−05 | 2.01E−02 |
| Actinobacteria | Actinobacteria | Actinomycetales | Unclassified | sf_3 | 1114 clone PENDANT-38 | week | 0.63 | 6.73E−05 | 3.18E−02 |
| Actinobacteria | Actinobacteria | Actinomycetales | Gordoniaceae | sf_1 | 1116 Gordona terrae | week | 0.61 | 1.18E−04 | 3.68E−02 |
| Actinobacteria | Actinobacteria | Actinomycetales | Actinosynnemataceae | sf_1 | 1125 *Actinokineospora diospyrosa* str. NRRL B-24047T | max TEMP | 0.6 | 1.53E−04 | 4.30E−02 |
| Actinobacteria | Actinobacteria | Actinomycetales | Actinosynnemataceae | sf_1 | 1125 *Actinokineospora diospyrosa* str. NRRL B-24047T | week | 0.63 | 7.42E−05 | 3.38E−02 |
| Actinobacteria | Actinobacteria | Actinomycetales | Streptomycetaceae | sf_1 | 1128 *Streptomyces* sp. str. YIM 80305 | week | 0.7 | 3.75E−06 | 1.18E−02 |
| Actinobacteria | Actinobacteria | Actinomycetales | Sporichthyaceae | sf_1 | 1223 *Sporichthya polymorpha* | mean TEMP | 0.61 | 1.42E−04 | 4.21E−02 |
| Actinobacteria | Actinobacteria | Actinomycetales | Sporichthyaceae | sf_1 | 1223 *Sporichthya polymorpha* | min MINTEMP | 0.61 | 1.50E−04 | 4.27E−02 |
| Actinobacteria | Actinobacteria | Actinomycetales | Sporichthyaceae | sf_1 | 1223 *Sporichthya polymorpha* | week | 0.7 | 4.39E−06 | 1.18E−02 |
| Actinobacteria | Actinobacteria | Actinomycetales | Microbacteriaceae | sf_1 | 1264 Waste-gas biofilter clone BIhi33 | mean TEMP | 0.61 | 1.47E−04 | 4.25E−02 |
| Actinobacteria | Actinobacteria | Actinomycetales | Microbacteriaceae | sf_1 | 1264 Waste-gas biofilter clone BIhi33 | week | 0.69 | 7.62E−06 | 1.18E−02 |
| Actinobacteria | Actinobacteria | Actinomycetales | Streptomycetaceae | sf_1 | 1344 *Streptomyces* species | max TEMP | 0.64 | 5.42E−05 | 2.84E−02 |
| Actinobacteria | Actinobacteria | Actinomycetales | Streptomycetaceae | sf_1 | 1344 *Streptomyces* species | mean TEMP | 0.62 | 9.56E−05 | 3.63E−02 |
| Actinobacteria | Actinobacteria | Actinomycetales | Thermomonosporaceae | sf_1 | 1406 *Actinomadura kijaniata* | week | 0.65 | 2.91E−05 | 2.29E−02 |
| Actinobacteria | Actinobacteria | Actinomycetales | Kineosporiaceae | sf_1 | 1424 Actinomycetaceae SR 139 | max VISIB | 0.6 | 1.70E−04 | 4.59E−02 |
| Actinobacteria | Actinobacteria | Actinomycetales | Kineosporiaceae | sf_1 | 1424 Actinomycetaceae SR 139 | week | 0.62 | 8.03E−05 | 3.50E−02 |
| Actinobacteria | Actinobacteria | Actinomycetales | Intrasporangiaceae | sf_1 | 1445 *Ornithinimicrobium humiphilum* str. DSM 12362 HKI 124 | week | 0.62 | 9.46E−05 | 3.63E−02 |
| Actinobacteria | Actinobacteria | Actinomycetales | Unclassified | sf_3 | 1514 uncultured human oral bacterium A11 | week | 0.69 | 7.08E−06 | 1.18E−02 |
| Actinobacteria | Actinobacteria | Actinomycetales | Pseudonocardiaceae | sf_1 | 1530 *Pseudonocardia thermophila* str. IMSNU 20112T | max TEMP | 0.64 | 5.10E−05 | 2.79E−02 |

TABLE S6-continued

Sub-families detected in Austin or San Antonio correlating significantly with environmental parameters.
All of the below are in the Domain of Bacteria

| Phylum | Class | Order | Family | Sub-family | taxon and representative organism name | Environ. factor | Correl. Coeff. | p value | BH adjusted p. value[a] |
|---|---|---|---|---|---|---|---|---|---|
| Actinobacteria | Actinobacteria | Actinomycetales | Pseudonocardiaceae | sf_1 | 1530 Pseudonocardia thermophila str. IMSNU 20112T | mean TEMP | 0.66 | 1.99E−05 | 1.97E−02 |
| Actinobacteria | Actinobacteria | Actinomycetales | Pseudonocardiaceae | sf_1 | 1530 Pseudonocardia thermophila str. IMSNU 20112T | min MINTEMP | 0.61 | 1.10E−04 | 3.63E−02 |
| Actinobacteria | Actinobacteria | Actinomycetales | Pseudonocardiaceae | sf_1 | 1530 Pseudonocardia thermophila str. IMSNU 20112T | min TEMP | 0.6 | 1.82E−04 | 4.73E−02 |
| Actinobacteria | Actinobacteria | Actinomycetales | Pseudonocardiaceae | sf_1 | 1530 Pseudonocardia thermophila str. IMSNU 20112T | week | 0.73 | 1.15E−06 | 5.92E−03 |
| Actinobacteria | Actinobacteria | Actinomycetales | Cellulomonaaceae | sf_1 | 1592 Lake Bogoria isolate 69B4 | week | 0.61 | 1.15E−04 | 3.63E−02 |
| Actinobacteria | Actinobacteria | Actinomycetales | Corynebacteriaceae | sf_1 | 1642 Corynebacterium otitidis | max TEMP | 0.62 | 8.87E−05 | 3.63E−02 |
| Actinobacteria | Actinobacteria | Actinomycetales | Corynebacteriaceae | sf_1 | 1642 Corynebacterium otitidis | mean TEMP | 0.64 | 4.12E−05 | 2.49E−02 |
| Actinobacteria | Actinobacteria | Actinomycetales | Corynebacteriaceae | sf_1 | 1642 Corynebacterium otitidis | min MINTEMP | 0.62 | 1.07E−04 | 3.63E−02 |
| Actinobacteria | Actinobacteria | Actinomycetales | Corynebacteriaceae | sf_1 | 1642 Corynebacterium otitidis | week | 0.63 | 5.53E−05 | 2.84E−02 |
| Actinobacteria | Actinobacteria | Actinomycetales | Dermabacteraceae | sf_1 | 1736 Brachybacterium rhamnosum LMG 19848T | max TEMP | 0.63 | 6.17E−05 | 3.09E−02 |
| Actinobacteria | Actinobacteria | Actinomycetales | Dermabacteraceae | sf_1 | 1736 Brachybacterium rhamnosum LMG 19848T | mean TEMP | 0.6 | 1.91E−04 | 4.90E−02 |
| Actinobacteria | Actinobacteria | Actinomycetales | Dermabacteraceae | sf_1 | 1736 Brachybacterium rhamnosum LMG 19848 T | week | 0.64 | 4.47E−05 | 2.62E−02 |
| Actinobacteria | Actinobacteria | Actinomycetales | Streptomycetaceae | sf_3 | 1743 Streptomyces scabiei str. DNK-G01 | week | 0.6 | 1.60E−04 | 4.38E−02 |
| Actinobacteria | Actinobacteria | Actinomycetales | Nocardiaceae | sf_1 | 1746 Nocardia corynebacteroides | week | 0.66 | 2.48E−05 | 2.21E−02 |
| Actinobacteria | Actinobacteria | Actinomycetales | Unclassified | sf_3 | 1806 French Polynesia: Tahiti clone 23 | max TEMP | 0.65 | 3.37E−05 | 2.29E−02 |
| Actinobacteria | Actinobacteria | Actinomycetales | Unclassified | sf_3 | 1806 French Polynesia: Tahiti clone 23 | mean TEMP | 0.66 | 1.97E−05 | 1.97E−02 |
| Actinobacteria | Actinobacteria | Actinomycetales | Micromonosporaceae | sf_1 | 1821 Catellatospora subsp. citrea str. IMSNU 22008T | max TEMP | 0.61 | 1.10E−04 | 3.63E−02 |
| Actinobacteria | Actinobacteria | Actinomycetales | Micromonosporaceae | sf_1 | 1821 Catellatospora subsp. citrea str. IMSNU 22008T | mean MINTEMP | 0.61 | 1.22E−04 | 3.72E−02 |
| Actinobacteria | Actinobacteria | Actinomycetales | Micromonosporaceae | sf_1 | 1821 Catellatospora subsp. citrea str. IMSNU 22008T | mean TEMP | 0.67 | 1.76E−05 | 1.97E−02 |
| Actinobacteria | Actinobacteria | Actinomycetales | Micromonosporaceae | sf_1 | 1821 Catellatospora subsp. citrea str. IMSNU 22008T | min MINTEMP | 0.7 | 4.92E−06 | 1.18E−02 |
| Actinobacteria | Actinobacteria | Actinomycetales | Micromonosporaceae | sf_1 | 1821 Catellatospora subsp. citrea str. IMSNU 22008T | min TEMP | 0.65 | 2.68E−05 | 2.29E−02 |
| Actinobacteria | Actinobacteria | Actinomycetales | Micromonosporaceae | sf_1 | 1821 Catellatospora subsp. citrea str. IMSNU 22008T | week | 0.62 | 8.24E−05 | 3.52E−02 |
| Actinobacteria | Actinobacteria | Rubrobacterales | Rubrobacteraceae | sf_1 | 1892 Sturt arid-zone soil clone 0319-7H2 | min MINTEMP | 0.62 | 8.51E−05 | 3.56E−02 |
| Actinobacteria | Actinobacteria | Rubrobacterales | Rubrobacteraceae | sf_1 | 1892 Sturt arid-zone soil clone 0319-7H2 | week | 0.68 | 9.19E−06 | 1.18E−02 |
| Actinobacteria | Actinobacteria | Actinomycetales | Actinosynnemataceae | sf_1 | 1984 Saccharothrix tangerinus str. MK27-91F2 | max TEMP | 0.68 | 8.01E−06 | 1.18E−02 |
| Actinobacteria | Actinobacteria | Actinomycetales | Actinosynnemataceae | sf_1 | 1984 Saccharothrix tangerinus str. MK27-91F2 | mean TEMP | 0.67 | 1.64E−05 | 1.97E−02 |
| Actinobacteria | Actinobacteria | Actinomycetales | Actinosynnemataceae | sf_1 | 1984 Saccharothrix tangerinus str. MK27-91F2 | week | 0.7 | 3.54E−06 | 1.18E−02 |
| Actinobacteria | Actinobacteria | Actinomycetales | Nocardiaceae | sf_1 | 1999 Rhodococcus fascians str. DFA7 | max TEMP | 0.61 | 1.14E−04 | 3.63E−02 |

TABLE S6-continued

Sub-families detected in Austin or San Antonio correlating significantly with environmental parameters.
All of the below are in the Domain of Bacteria

| Phylum | Class | Order | Family | Sub-family | taxon and representative organism name | Environ. factor | Correl. Coeff. | p value | BH adjusted p. value[a] |
|---|---|---|---|---|---|---|---|---|---|
| Actinobacteria | Actinobacteria | Actinomycetales | Propionibacteriaceae | sf_1 | 2023 Propionibacterium propionicum str. DSM 43307T | week | 0.62 | 9.19E−05 | 3.63E−02 |
| Actinobacteria | Actinobacteria | Actinomycetales | Streptosporangiaceae | sf_1 | 2037 Nonomuraea terrinata str. DSM 44505 | week | 0.61 | 1.13E−04 | 3.63E−02 |
| Firmicutes | Bacilli | Bacillales | Thermoactinomycetaceae | sf_1 | 3619 Thermoactinomyces intermedius str. ATCC 33205T | range MINTEMP | 0.65 | 3.41E−05 | 2.29E−02 |
| Cyanobacteria | Cyanobacteria | Symploca | Unclassified | sf_1 | 5165 Symploca atlantica str. PCC 8002 | week | 0.63 | 6.84E−05 | 3.18E−02 |
| Bacteroidetes | Sphingobacteria | Sphingobacteriales | Crenotrichaceae | sf_11 | 5491 Austria: Lake Gossenkoellesee clone GKS2-106 | mean TEMP | 0.61 | 1.15E−04 | 3.63E−02 |
| Bacteroidetes | Sphingobacteria | Sphingobacteriales | Crenotrichaceae | sf_11 | 5491 Austria: Lake Gossenkoellesee clone GKS2-106 | week | 0.63 | 6.62E−05 | 3.18E−02 |
| Bacteroidetes | Sphingobacteria | Sphingobacteriales | Flexibacteraceae | sf_19 | 5866 Taxeobacter ocellatus str. Myx2105 | week | 0.62 | 1.08E−04 | 3.63E−02 |
| Bacteroidetes | Bacteroidetes | Bacteroidales | Prevotellaceae | sf_1 | 6047 deep marine sediment clone MB-A2-107 | week | 0.62 | 9.52E−05 | 3.63E−02 |
| Bacteroidetes | Sphingobacteria | Sphingobacteriales | Crenotrichaceae | sf_11 | 6171 Bifissio spartinae str. AS1.1762 | max PM2.5 | −0.62 | 9.95E−05 | 3.63E−02 |
| Bacteroidetes | Sphingobacteria | Sphingobacteriales | Crenotrichaceae | sf_11 | 6171 Bifissio spartinae str. AS1.1762 | max VISIB | 0.62 | 1.09E−04 | 3.63E−02 |
| Bacteroidetes | Sphingobacteria | Sphingobacteriales | Crenotrichaceae | sf_11 | 6171 Bifissio spartinae str. AS1.1762 | range PM2.5 | −0.65 | 2.86E−05 | 2.29E−02 |
| Bacteroidetes | Sphingobacteria | Sphingobacteriales | Crenotrichaceae | sf_11 | 6171 Bifissio spartinae str. AS1.1762 | week | 0.61 | 1.25E−04 | 3.76E−02 |
| Proteobacteria | Alphaproteobacteria | Sphingomonadales | Sphingomonadaceae | sf_1 | 6808 PCB-polluted soil clone WD267 | mean TEMP | 0.63 | 7.73E−05 | 3.45E−02 |
| Proteobacteria | Alphaproteobacteria | Sphingomonadales | Sphingomonadaceae | sf_1 | 6808 PCB-polluted soil clone WD267 | week | 0.69 | 5.54E−06 | 1.18E−02 |
| Proteobacteria | Alphaproteobacteria | Sphingomonadales | Sphingomonadaceae | sf_1 | 7132 Sphingomonas sp. K101 | min SLP | 0.64 | 5.16E−05 | 2.79E−02 |
| Proteobacteria | Alphaproteobacteria | Sphingomonadales | Sphingomonadaceae | sf_1 | 7132 Sphingomonas sp. K101 | week | 0.75 | 2.74E−07 | 2.81E−03 |
| Proteobacteria | Alphaproteobacteria | Bradyrhizobiales | Unclassified | sf_1 | 7255 Pleomorphomonas oryzae str. B-32 | max TEMP | 0.65 | 3.57E−05 | 2.29E−02 |
| Proteobacteria | Alphaproteobacteria | Bradyrhizobiales | Unclassified | sf_1 | 7255 Pleomorphomonas oryzae str. B-32 | mean TEMP | 0.64 | 4.62E−05 | 2.63E−02 |
| Proteobacteria | Alphaproteobacteria | Sphingomonadales | Sphingomonadaceae | sf_1 | 7344 rhizosphere soil RSI-21 | week | 0.68 | 8.96E−06 | 1.18E−02 |
| Proteobacteria | Alphaproteobacteria | Sphingomonadales | Sphingomonadaceae | sf_1 | 7411 Sphingomonas adhaesiva | min SLP | 0.66 | 2.01E−05 | 1.97E−02 |
| Proteobacteria | Alphaproteobacteria | Sphingomonadales | Sphingomonadaceae | sf_1 | 7411 Sphingomonas adhaesiva | week | 0.74 | 6.42E−07 | 4.39E−03 |
| Proteobacteria | Alphaproteobacteria | Rhodobacterales | Rhodobacteraceae | sf_1 | 7527 clone CTD56B | mean TEMP | 0.61 | 1.44E−04 | 4.23E−02 |
| Proteobacteria | Alphaproteobacteria | Sphingomonadales | Sphingomonadaceae | sf_1 | 7555 derived microbial 'pearl'-community clone sipK48 | week | 0.6 | 1.60E−04 | 4.38E−02 |
| Proteobacteria | Alphaproteobacteria | Bradyrhizobiales | Methylobacteriaceae | sf_1 | 7593 Methylobacterium organophilum | max TEMP | 0.65 | 3.53E−05 | 2.29E−02 |
| Proteobacteria | Alphaproteobacteria | Bradyrhizobiales | Methylobacteriaceae | sf_1 | 7593 Methylobacterium organophilum | mean TEMP | 0.62 | 9.87E−05 | 3.63E−02 |
| Proteobacteria | Alphaproteobacteria | Bradyrhizobiales | Methylobacteriaceae | sf_1 | 7593 Methylobacterium organophilum | week | 0.68 | 8.06E−06 | 1.18E−02 |
| Proteobacteria | Alphaproteobacteria | Devosia | Unclassified | sf_1 | 7626 Devosia neptuniae str. J1 | week | 0.6 | 1.80E−04 | 4.73E−02 |
| Proteobacteria | Betaproteobacteria | Burkholderiales | Comamonadaceae | sf_1 | 7786 unidentified alpha proteobacterium | mean TEMP | 0.65 | 3.45E−05 | 2.29E−02 |
| Proteobacteria | Betaproteoteria | Burkholderiales | Burkholderiaceae | sf_1 | 7899 Burkholderia andropogonis | week | 0.65 | 3.43E−05 | 2.29E−02 |
| Proteobacteria | Gammaproteobacteria | Unclassified | Unclassified | sf_3 | 8759 Agricultural soil SC-I-87 | max TEMP | 0.6 | 1.74E−04 | 4.63E−02 |
| Proteobacteria | Gammaproteobacteria | Pseudomonadales | Pseudomonadaceae | sf_1 | 9389 Pseudomonas oleovorans | min SLP | 0.68 | 8.57E−06 | 1.18E−02 |

TABLE S6-continued

Sub-families detected in Austin or San Antonio correlating significantly with environmental parameters.
All of the below are in the Domain of Bacteria

| Phylum | Class | Order | Family | Sub-family | taxon and representative organism name | Environ. factor | Correl. Coeff. | p value | BH adjusted p. value[a] |
|---|---|---|---|---|---|---|---|---|---|
| Proteobacteria | Gammaproteobacteria | Pseudomonadales | Pseudomonadaceae | sf_1 | 9389 *Pseudomonas oleovorans* | week | 0.83 | 1.03E−09 | 2.11E−05 |

[a] P-value is adjusted for multiple comparisons using false discovery rate controlling procedure (S18).

TABLE S7

Bacterial sub-families detected (92% or greater of probes in probe set positive) most frequently over 17 week study.

| Most frequently detected 16S rRNA gene sequences | AU | SA |
|---|---|---|
| Bacteria; Acidobacteria; Acidobacteria; Acidobacteriales; Acidobacteriaceae; sf_14 | 17 | 17 |
| Bacteria; Acidobacteria; Acidobacteria-6; Unclassified; Unclassified; sf_1 | *16* | 17 |
| Bacteria; Acidobacteria; Solibacteres; Unclassified; Unclassified; sf_1 | 17 | 17 |
| Bacteria; Actinobacteria; Actinobacteria; Actinomycetales; Cellulomonadaceae; sf_1 | 17 | 17 |
| Bacteria; Actinobacteria; Actinobacteria; Actinomycetales; Corynebacteriaceae; sf_1 | *16* | 17 |
| Bacteria; Actinobacteria; Actinobacteria; Actinomycetales; Gordoniaceae; sf_1 | 17 | 17 |
| Bacteria; Actinobacteria; Actinobacteria; Actinomycetales; Kineosporiaceae; sf_1 | 17 | 17 |
| Bacteria; Actinobacteria; Actinobacteria; Actinomycetales; Microbacteriaceae; sf_1 | *16* | 17 |
| Bacteria; Actinobacteria; Actinobacteria; Actinomycetales; Micrococcaceae; sf_1 | 17 | 17 |
| Bacteria; Actinobacteria; Actinobacteria; Actinomycetales; Micromonosporaceae; sf_1 | 17 | 17 |
| Bacteria; Actinobacteria; Actinobacteria; Actinomycetales; Mycobacteriaceae; sf_1 | 17 | 17 |
| Bacteria; Actinobacteria; Actinobacteria; Actinomycetales; Nocardiaceae; sf_1 | 17 | 17 |
| Bacteria; Actinobacteria; Actinobacteria; Actinomycetales; Promicromonosporaceae; sf_1 | 17 | 17 |
| Bacteria; Actinobacteria; Actinobacteria; Actinomycetales; Pseudonocardiaceae; sf_1 | *16* | 17 |
| Bacteria; Actinobacteria; Actinobacteria; Actinomycetales; Streptomycetaceae; sf_1 | 17 | 17 |
| Bacteria; Actinobacteria; Actinobacteria; Actinomycetales; Thermomonosporaceae; sf_1 | *16* | 17 |
| Bacteria; Actinobacteria; Actinobacteria; Actinomycetales; Unclassified; sf_3 | 17 | 17 |
| Bacteria; Actinobacteria; Actinobacteria; Rubrobacterales; Rubrobacteraceae; sf_1 | *16* | 17 |
| Bacteria; Actinobacteria; Actinobacteria; Unclassified; Unclassified; sf_1 | *16* | 17 |
| Bacteria; Actinobacteria; BD2-10 group; Unclassified; Unclassified; sf_2 | 17 | *16* |
| Bacteria; Bacteroidetes; Sphingobacteria; Sphingobacteriales; Unclassified; sf_3 | *16* | 17 |
| Bacteria; Chloroflexi; Anaerolineae; Chloroflexi-1a; Unclassified; sf_1 | *16* | 17 |
| Bacteria; Chloroflexi; Anaerolineae; Unclassified; Unclassified; sf_9 | *16* | 17 |
| Bacteria; Chloroflexi; Dehalococcoidetes; Unclassified; Unclassified; sf_1 | *16* | 17 |
| Bacteria; Cyanobacteria; Cyanobacteria; Chloroplasts; Chloroplasts; sf_5 | 17 | 17 |
| Bacteria; Cyanobacteria; Cyanobacteria; Plectonema; Unclassified; sf_1 | *16* | 17 |
| Bacteria; Cyanobacteria; Unclassified; Unclassified; Unclassified; sf_5 | *16* | 17 |
| Bacteria; Firmicutes; Bacilli; Bacillales; Bacillaceae; sf_1 | 17 | 17 |
| Bacteria; Firmicutes; Bacilli; Bacillales; Halobacillaceae; sf_1 | 17 | 17 |
| Bacteria; Firmicutes; Bacilli; Bacillales; Paenibacillaceae; sf_1 | *16* | 17 |
| Bacteria; Firmicutes; Bacilli; Lactobacillales; Enterococcaceae; sf_1 | 17 | 17 |
| Bacteria; Firmicutes; Bacilli; Lactobacillales; Streptococcaceae; sf_1 | *16* | 17 |
| Bacteria; Firmicutes; Catabacter; Unclassified; Unclassified; sf_1 | *16* | 17 |
| Bacteria; Firmicutes; Clostridia; Clostridiales; Clostridiaceae; sf_12 | 17 | 17 |
| Bacteria; Firmicutes; Clostridia; Clostridiales; Lachnospiraceae; sf_5 | 17 | 17 |
| Bacteria; Firmicutes; Clostridia; Clostridiales; Peptococc/Acidaminococc; sf_11 | 17 | 17 |
| Bacteria; Firmicutes; Clostridia; Clostridiales; Peptostreptococcaceae; sf_5 | 17 | 17 |
| Bacteria; Firmicutes; Clostridia; Clostridiales; Unclassified; sf_17 | *16* | 17 |
| Bacteria; Firmicutes; Unclassified; Unclassified; Unclassified; sf_8 | *16* | 17 |
| Bacteria; Nitrospira; Nitrospira; Nitrospirales; Nitrospiraceae; sf_1 | 17 | *16* |
| Bacteria; OP3; Unclassified; Unclassified; Unclassified; sf_4 | *16* | 17 |
| Bacteria; Proteobacteria; Alphaproteobacteria; Acetobacterales; Acetobacteraceae; sf_1 | 17 | *16* |
| Bacteria; Proteobacteria; Alphaproteobacteria; Azospirillales; Unclassified; sf_1 | *16* | 17 |
| Bacteria; Proteobacteria; Alphaproteobacteria; Bradyrhizobiales; Beijerinck/Rhodoplan/Methylocyst; sf_3 | 17 | 17 |
| Bacteria; Proteobacteria; Alphaproteobacteria; Bradyrhizobiales; Bradyrhizobiaceae; sf_1 | 17 | 17 |
| Bacteria; Proteobacteria; Alphaproteobacteria; Bradyrhizobiales; Hyphomicrobiaceae; sf_1 | 17 | 17 |
| Bacteria; Proteobacteria; Alphaproteobacteria; Bradyrhizobiales; Methylobacteriaceae; sf_1 | *16* | 17 |
| Bacteria; Proteobacteria; Alphaproteobacteria; Ellin314/wr0007; Unclassified; sf_1 | *16* | 17 |
| Bacteria; Proteobacteria; Alphaproteobacteria; Rhizobiales; Bradyrhizobiaceae; sf_1 | *16* | 17 |
| Bacteria; Proteobacteria; Alphaproteobacteria; Rhizobiales; Phyllobacteriaceae; sf_1 | 17 | 17 |
| Bacteria; Proteobacteria; Alphaproteobacteria; Rhizobiales; Unclassified; sf_1 | *16* | 17 |
| Bacteria; Proteobacteria; Alphaproteobacteria; Rhodobacterales; Rhodobacteraceae; sf_1 | 17 | 17 |
| Bacteria; Proteobacteria; Alphaproteobacteria; Rickettsiales; Unclassified; sf_1 | 17 | 17 |
| Bacteria; Proteobacteria; Alphaproteobacteria; Sphingomonadales; Sphingomonadaceae; sf_1 | 17 | 17 |
| Bacteria; Proteobacteria; Alphaproteobacteria; Sphingomonadales; Sphingomonadaceae; sf_15 | 17 | 17 |
| Bacteria; Proteobacteria; Alphaproteobacteria; Unclassified; Unclassified; sf_6 | 17 | 17 |
| Bacteria; Proteobacteria; Betaproteobacteria; Burkholderiales; Alcaligenaceae; sf_1 | *16* | 17 |
| Bacteria; Proteobacteria; Betaproteobacteria; Burkholderiales; Burkholderiaceae; sf_1 | *16* | 17 |
| Bacteria; Proteobacteria; Betaproteobacteria; Burkholderiales; Comamonadaceae; sf_1 | *16* | 17 |
| Bacteria; Proteobacteria; Betaproteobacteria; Burkholderiales; Oxalobacteraceae; sf_1 | 17 | 17 |
| Bacteria; Proteobacteria; Betaproteobacteria; Burkholderiales; Ralstoniaceae; sf_1 | *16* | 17 |
| Bacteria; Proteobacteria; Betaproteobacteria; Methylophilales; Methylophilaceae; sf_1 | *16* | 17 |

TABLE S7-continued

Bacterial sub-families detected (92% or greater of probes in probe set positive) most frequently over 17 week study.

| Most frequently detected 16S rRNA gene sequences | AU | SA |
|---|---|---|
| Bacteria; Proteobacteria; Betaproteobacteria; Rhodocyclales; Rhodocyclaceae; sf_1 | *16* | 17 |
| Bacteria; Proteobacteria; Betaproteobacteria; Unclassified; Unclassified; sf_3 | 17 | 17 |
| Bacteria; Proteobacteria; Deltaproteobacteria; Syntrophobacterales; Syntrophobacteraceae; sf_1 | *16* | 17 |
| Bacteria; Proteobacteria; Epsilonproteobacteria; Campylobacterales; Campylobacteraceae; sf_3 | 17 | 17 |
| Bacteria; Proteobacteria; Epsilonproteobacteria; Campylobacterales; Helicobacteraceae; sf_3 | 17 | 17 |
| Bacteria; Proteobacteria; Epsilonproteobacteria; Campylobacterales; Unclassified; sf_1 | 17 | 17 |
| Bacteria; Proteobacteria; Gammaproteobacteria; Alteromonadales; Alteromonadaceae; sf_1 | *16* | 17 |
| Bacteria; Proteobacteria; Gammaproteobacteria; Chromatiales; Chromatiaceae; sf_1 | *16* | 17 |
| Bacteria; Proteobacteria; Gammaproteobacteria; Enterobacteriales; Enterobacteriaceae; sf_1 | *16* | 17 |
| Bacteria; Proteobacteria; Gammaproteobacteria; Enterobacteriales; Enterobacteriaceae; sf_6 | 17 | 17 |
| Bacteria; Proteobacteria; Gammaproteobacteria; Legionellales; Unclassified; sf_1 | 17 | 17 |
| Bacteria; Proteobacteria; Gammaproteobacteria; Legionellales; Unclassified; sf_3 | *16* | 17 |
| Bacteria; Proteobacteria; Gammaproteobacteria; Pseudomonadales; Moraxellaceae; sf_3 | *16* | 17 |
| Bacteria; Proteobacteria; Gammaproteobacteria; Pseudomonadales; Pseudomonadaceae; sf_1 | *16* | 17 |
| Bacteria; Proteobacteria; Gammaproteobacteria; Unclassified; sf_3 | 17 | 17 |
| Bacteria; Proteobacteria; Gammaproteobacteria; Xanthomonadales; Xanthomonadaceae; sf_3 | 17 | 17 |
| Bacteria; TM7; TM7-3; Unclassified; Unclassified; sf_1 | *16* | 17 |
| Bacteria; Unclassified; Unclassified; Unclassified; sf_148 | *16* | 17 |
| Bacteria; Unclassified; Unclassified; Unclassified; sf_160 | 17 | 17 |
| Bacteria; Verrucomicrobia; Verrucomicrobiae; Verrucomicrobiales; Verrucomicrobiaceae; sf_7 | 17 | 17 |
| Number of sub-families detected in all samples over 17 week period | 43 | 80 |

Italic text indicates sub-families not found in all 17 weeks.
AU = Austin, SA = San Antonio.

TABLE S8

Bacterial sub-families containing pathogens of public health and bioterrorism significance and their relatives that were detected in aerosols over the 17 week monitoring period.

| Pathogens and relatives | taxon # | Austin Weeks detected | Austin % of weeks | San Antonio Weeks detected | San Antonio % of weeks |
|---|---|---|---|---|---|
| *Bacillus anthracis* | | | | | |
| *Bacillus cohnii, B. psychrosaccharolyticus, B. benzoevorans* | 3439 | 17 | 100.0 | 17 | 100.0 |
| *Bacillus megaterium* | 3550 | 11 | 64.7 | 12 | 70.6 |
| *Bacillus horikoshii* | 3904 | 9 | 52.9 | 14 | 82.4 |
| *Bacillus litoralis, B. macroides, B. psychrosaccharolyticus* | 3337 | 5 | 29.4 | 8 | 47.1 |
| *Staphylococcus saprophyticus, S. xylosus, S. cohnii* | 3659 | 7 | 41.2 | 15 | 88.2 |
| *Bacillus anthracis, cereus, thuringiensis, mycoides* + others | 3262 | 0 | 0.0 | 1 | 5.9 |
| *Rickettsia prowazekii - rickettsii* | | | | | |
| *Rickettsia australis, R. eschlimannii, R. typhi, R. tarasevichiae* + others | 7556 | 2 | 11.8 | 5 | 29.4 |
| *Rickettsia prowazekii* | 7114 | 0 | 0.0 | 0 | 0.0 |
| *Rickettsia rickettsii, R. japonica, R. honei* + others | 6809 | 4 | 23.5 | 10 | 58.8 |
| *Burkholderia mallei - pseudomallei* | | | | | |
| *Burkholderia pseudomallei, B. thailandensis* | 7870 | 10 | 58.8 | 14 | 82.4 |
| *Burkholderia mallei* | 7747 | 10 | 58.8 | 8 | 47.1 |
| *Burkholderia pseudomallei, Burkholderia cepacia, B. tropica, B. gladioli, B. stabilis, B. plantarii* + others | 8097 | 13 | 76.5 | 15 | 88.2 |
| *Clostridum botulinum - perfringens* | | | | | |
| *Clostridium butyricum, C. baratii, C. sardiniense* + others | 4598 | 3 | 17.6 | 10 | 58.8 |
| *Clostridium botulinum* type C | 4587 | 2 | 11.8 | 4 | 23.5 |
| *Clostridium perfringens* | 4576 | 1 | 5.9 | 1 | 5.9 |
| *Clostridium botulinum* type G | 4575 | 3 | 17.6 | 7 | 41.2 |
| *Clostridium botulinum* types B and E | 4353 | 0 | 0.0 | 0 | 0.0 |
| *Francisella tularensis* | | | | | |
| *Tilapia* parasite | 9554 | 1 | 5.9 | 2 | 11.8 |
| *Francisella tularensis* | 9180 | 0 | 0.0 | 0 | 0.0 |

TABLE S9

Distribution of array taxa among Bacterial and Archaeal phyla.

| Phyla | Numbers of taxa in phylum represented on array |
|---|---|
| Archaea | |
| Crenarchaeota | 79 |
| Euryarchaeota | 224 |
| Korarchaeota | 3 |
| YNPFFA | 1 |
| Archaeal taxa subtotal | 307 |
| Bacteria | |
| 1959 group | 1 |
| Acidobacteria | 98 |
| Actinobacteria | 810 |
| AD3 | 1 |
| Aquificae | 19 |
| Bacteroidetes | 880 |
| BRC1 | 3 |
| Caldithrix | 2 |
| Chlamydiae | 27 |
| Chlorobi | 21 |
| Chloroflexi | 117 |
| Chrysiogenetes | 1 |
| Coprothermobacteria | 3 |
| Cyanobacteria | 202 |
| Deferribacteres | 5 |
| Deinococcus-Thermus | 18 |
| Dictyoglomi | 5 |
| DSS1 | 2 |
| EM3 | 2 |
| Fibrobacteres | 4 |
| Firmicutes | 2012 |
| Fusobacteria | 29 |
| Gemmatimonadetes | 15 |
| LD1PA group | 1 |
| Lentisphaerae | 8 |
| marine group A | 5 |
| Natronoanaerobium | 7 |
| NC10 | 4 |
| Nitrospira | 29 |
| NKB19 | 2 |
| OD1 | 4 |
| OD2 | 6 |
| OP1 | 5 |
| OP10 | 12 |
| OP11 | 20 |
| OP3 | 5 |
| OP5 | 3 |
| OP8 | 8 |
| OP9/JS1 | 12 |
| OS-K | 2 |
| OS-L | 1 |
| Planctomycetes | 182 |
| Proteobacteria | 3170 |
| SPAM | 2 |
| Spirochaetes | 150 |
| SR1 | 4 |
| Synergistes | 19 |
| Termite group 1 | 6 |
| Thermodesulfobacteria | 4 |
| Thermotogae | 15 |
| TM6 | 5 |
| TM7 | 45 |
| Unclassified | 329 |
| Verrucomicrobia | 78 |
| WS1 | 2 |
| WS3 | 7 |
| WS5 | 1 |
| WS6 | 4 |
| Bacterial taxa subtotal | 8434 |
| Total taxa | 8741 |

EQUIVALENTS

The foregoing written specification is considered to be sufficient to enable one skilled in the art to practice the present embodiments. The foregoing description and Examples detail certain preferred embodiments and describes the best mode contemplated by the inventors. It will be appreciated, however, that no matter how detailed the foregoing may appear in text, the present embodiments may be practiced in many ways and the present embodiments should be construed in accordance with the appended claims and any equivalents thereof.

The term "comprising" is intended herein to be open-ended, including not only the recited elements, but further encompassing any additional elements.

What is claimed is:

1. A method comprising:
applying a sample comprising nucleic acids derived from a plurality of microorganisms representing a plurality of operational taxonomic units (OTUs) to a system, the system comprising
(i) a first probe set comprising a plurality of different first nucleic acid probes, each of which is complementary to a 16S rRNA or rDNA sequence that is present only within a first OTU,
(ii) a second probe set comprising a plurality of different second nucleic acid probes, each of which is complementary to a 16S rRNA or rDNA sequence that is present in more than one OTU but collectively are present only in a second OTU, wherein the second OTU is different than the first OTU, and
(iii) a third probe set consisting of a plurality of different third nucleic acid probes for detecting a third OTU, wherein the third nucleic acid probes are complementary to 16S rRNA or rDNA sequences collectively present in the third OTU and another OTU, and are selected to minimize the number of putative cross-reactive OTUs, wherein the third OTU is different from the second OTU and the first OTU; and
detecting hybridization between the nucleic acids derived from the plurality of microorganisms and the first, second and third probe sets, and identifying the presence and/or quantity of microorganisms from the first, second and third OTUs based on the hybridization.

2. The method of claim 1, wherein the plurality of microorganisms comprises bacteria or archaea.

3. The method of claim 1, wherein the system further comprises more than one mismatch probe for each of the nucleic acid probes complementary to 16S rRNA or rDNA sequences, wherein each mismatch probe differs from the nucleic acid probe to which it corresponds at one or more nucleotide bases.

4. The method of claim 1, wherein the OTUs identified in presence and/or quantity are the most metabolically active organisms in the sample.

5. A method comprising:
applying a sample comprising nucleic acids derived from a plurality of microorganisms representing a plurality of operational taxonomic units (OTUs) to a system, the system comprising:
(i) a first probe set comprising at least 11 different first nucleic acid probes, each of said first nucleic acid probes being complementary to a 16S rRNA or rDNA sequence present only in a first OTU,
(ii) a second probe set comprising at least 11 different second nucleic acid probes, each of said second nucleic acid probes being complementary to a 16S rRNA or rDNA sequence present in a plurality of OTUs but collectively are present only in a second OTU, wherein the second OTU is different than the first OTU,
(iii) a third probe set consisting of at least 11 different nucleic acid probes for detecting a third OTU, wherein the third nucleic acid probes are complementary to 16S rRNA or rDNA sequences collectively present in the third OTU and another OTU, wherein the third OTU is different from the second OTU and the first OTU, wherein the different third nucleic acid probes are selected to minimize the number of putative cross-reactive OTUs; and
detecting hybridization between the nucleic acids derived from the plurality of microorganisms and the first, second and third probe sets, and identifying the presence and/or the quantity of microorganisms from the first, second and third OTUs based on the hybridization.

6. The method of claim 5, wherein the identification is made with a level of confidence of about 90% or higher.

7. The method of claim 6, wherein said level of confidence is 95% or higher.

8. The method of claim 6, wherein said level of confidence is 98% or higher.

9. The method of claim 1 or 5, wherein said sample is an environmental sample.

10. The method of claim 1 or 5, wherein said sample is a clinical sample.

11. The method of claim 10, wherein said clinical sample comprises at least one of tissue, skin, bodily fluid, or blood.

12. The method of claim 10, wherein said clinical sample is a lung sample, a gut sample, an ear sample, a nose sample, a throat sample, or a digestive system sample.

13. The method of claim 1 or 5, wherein said plurality of nucleic acid probes are arranged in an array.

14. The method of claim 1 or 5, wherein said system is capable of detecting about 9000 different OTUs.

15. The method of claim 1 or 5, wherein said nucleic acids are selected from the group consisting of: DNA, RNA, DNA from amplified products, and rRNA.

16. The method of claim 1 or 5, wherein all demarcated bacterial and archaeal orders are represented by said nucleic acid probes.

17. The method of claim 1 or 5, wherein, for a majority of OTUs that can be detected by said system, said nucleic acid probes are complementary to 16S rRNA sequences that have only been identified within a single OTU.

18. The method of claim 1 or 5, further comprising quantifying rRNA molecules present in said sample.

19. The method of claim 1 or 5, wherein at least a subset of said first, second or third nucleic acid probes comprise sequences complementary to 16S rRNA or rDNA sequence fragments, wherein only partial gene sequence is known.

20. The method of claim 1 wherein said system comprises from about 2 to about 200 first, second or third nucleic acid probes complementary to 16S rRNA or rDNA sequences for each of said OTUs.

21. The method of claim 12, wherein said clinical sample is a gut sample.

22. The method of claim 1 or 5, wherein each probe is from about 20 to about 30 by long.

23. The method of claim 1 or 5, wherein each of the probes is a 25-mer.

24. The method of claim 1 or 5, wherein said system further comprises a mismatch probe for each of the plurality of probes in the first set of probes, second set of probes and third set of probes, wherein each of the mismatch probes differs from its respective probe at one or more nucleotide bases based.

25. The method of claim 1 or 5, wherein an OTU is considered present in the sample when at least a threshold percentage of a plurality of probe pairs assigned to it are positive.

26. The method of claim 25, wherein the threshold percentage is >92%.

27. The method of claim 1 or 5, wherein an OTU consists of sequences having up to 3% sequence divergence.

28. A method comprising:
applying a sample comprising nucleic acids derived from a plurality of microorganisms representing a plurality of operational taxonomic units (OTUs) to a system, the system comprising (i) a first probe set comprising a plurality of different first nucleic acid probes, each of which is complementary to a 16S rRNA or rDNA sequence that is present only within a first OTU, (ii) a second probe set comprising a plurality of different second nucleic acid probes, each of which is complementary to a 16S rRNA or rDNA sequence that is present in more than one OTU but collectively are present only in a second OTU, wherein the second OTU is different than the first OTU, and (iii) a third probe set consisting of a plurality of different third nucleic acid probes for detecting a third OTU, wherein the third nucleic acid probes are complementary to 16S rRNA or rDNA sequences collectively present in the second OTU and the third OTU, and are selected to minimize the number of putative cross-reactive OTUs, wherein the third OTU is different from the second OTU and the first OTU; and detecting hybridization between the nucleic acids derived from the plurality of microorganisms and the first, second and third probe sets, and identifying the presence and/or the quantity of microorganisms from the first, second and third OTUs based on the hybridization.

\* \* \* \* \*

UNITED STATES PATENT AND TRADEMARK OFFICE
CERTIFICATE OF CORRECTION

PATENT NO. : 8,771,940 B2
APPLICATION NO. : 12/474204
DATED : July 8, 2014
INVENTOR(S) : Gary L. Andersen It is certified that error appears in the above-identified patent and that said Letters Patent is hereby corrected as shown below:

Column 2 (title page 1, item 56) line 48, References Cited under Other Publications, change "2002." to --2002).--.

Column 2 (title page 3, item 56) line 13, References Cited under Other Publications, change "oligonnucleotide" to --oligonucleotide--.

In the Drawings

Sheet 1 of 4 (FIG. 1) line 6 (X-axis), Change "20" to --200--.

Figure 3:
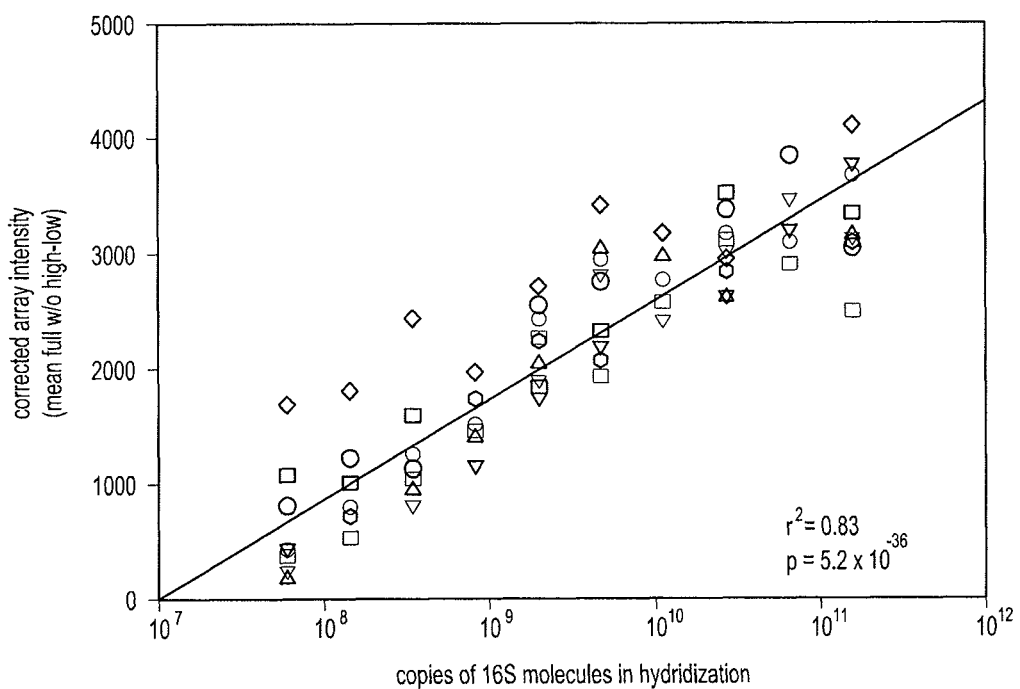
FIG. 3 is a graph showing a Latin square assessment of 16S rRNA gene sequence quantitation by microarray.
Figure 4:
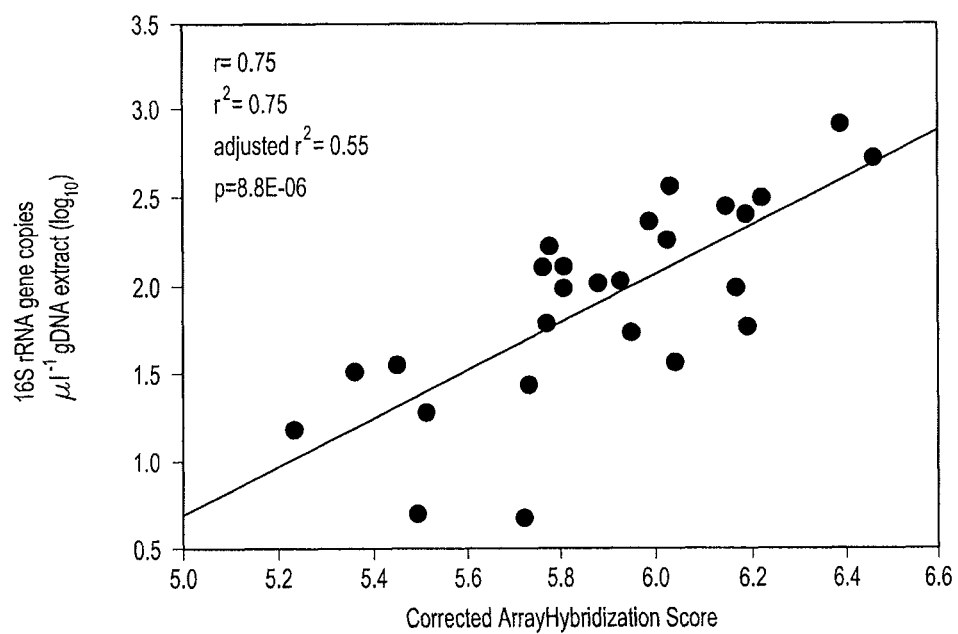
FIG. 4 is a graph showing comparison of real-time PCR and array monitoring of *Pseudomonas oleovorans* density in aerosol samples from San Antonio. Corrected Array Hybridization Score is the ln(intensity) normalized by internal spikes as described under Normalization.

Sheet 3 of 4 (FIG. 1) line 4 (FIG. 3), Change "Dehalococoides" to --Dehalococcoides--.

In the Specification

Column 1 at line 19, Change "DE-AC03-76SF00098" to --HSSCHQ04X00037--.

Column 1 at line 20, Change "AC0" to --AC02--.

Column 2 at line 31, Change "1" to --11--.

Column 5 at line 16, Change "specific" to --specific,--.

Column 8 at line 31, Change "archacal" to --archaeal--.

Column 10 at line 22, Change "Calanese)." to --Celanese).--.

Column 10 at line 56, Change "1x" to --1X--.

Column 11 at line 1, Change "1x" to --1X--.

Column 11 at line 5, Change "see" to --sec--.

Column 13 at line 45, Change "1xiQ" to --1XiQ--.

Column 14 at line 24, Change "Brady" to --Bray--.

Column 14 at line 34, Change "Chaot" to --Chao 1--.

Columns 37-38 at lines 19-20, Change "Cellulomonaaceae" to --Cellulomonadaceae--.

Signed and Sealed this
Twenty-fourth Day of February, 2015

Michelle K. Lee
*Deputy Director of the United States Patent and Trademark Office*

CERTIFICATE OF CORRECTION (continued)
U.S. Pat. No. 8,771,940 B2

In the Claims

Column 56 line 47, Claim 22, Change "by" to --bp--.

Column 56 line 54-55, Claim 24, After "bases" delete "based".

UNITED STATES PATENT AND TRADEMARK OFFICE
CERTIFICATE OF CORRECTION

| | | |
|---|---|---|
| PATENT NO. | : 8,771,940 B2 | Page 1 of 1 |
| APPLICATION NO. | : 12/474204 | |
| DATED | : July 8, 2014 | |
| INVENTOR(S) | : Andersen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this
Third Day of May, 2016

Michelle K. Lee
*Director of the United States Patent and Trademark Office*